(12) United States Patent
Etkin et al.

(10) Patent No.: US 11,526,808 B2
(45) Date of Patent: Dec. 13, 2022

(54) MACHINE LEARNING BASED GENERATION OF ONTOLOGY FOR STRUCTURAL AND FUNCTIONAL MAPPING

(71) Applicants: The Board of Trustees of the Leland Stanford Junior University, Stanford, CA (US); The United States Government as Represented by the Department of Veterans Affairs, Washington, DC (US)

(72) Inventors: Amit Etkin, Palo Alto, CA (US); Elizabeth Beam, Palo Alto, CA (US)

(73) Assignees: The Board of Trustees of the Leland Stanford Junior University, Stanford, CA (US); The United States Government as Represented by the Department of Veterans Affairs, Washington, DC (US)

( * ) Notice: Subject to any disclaimer, the term of this patent is extended or adjusted under 35 U.S.C. 154(b) by 328 days.

(21) Appl. No.: 16/888,530

(22) Filed: May 29, 2020

(65) Prior Publication Data
US 2020/0401938 A1  Dec. 24, 2020

Related U.S. Application Data

(60) Provisional application No. 62/853,958, filed on May 29, 2019.

(51) Int. Cl.
*G06K 9/00* (2022.01)
*G06N 20/00* (2019.01)
(Continued)

(52) U.S. Cl.
CPC .......... *G06N 20/00* (2019.01); *G06K 9/6223* (2013.01); *G06K 9/6277* (2013.01); *G06N 3/02* (2013.01);
(Continued)

(58) Field of Classification Search
CPC .......... G06N 20/00; G06N 3/02; G06N 5/042; G06N 5/046; G06N 3/08; G06N 3/0454;
(Continued)

(56) References Cited

U.S. PATENT DOCUMENTS

| 10,546,233 B1 * | 1/2020 | Bhattacharyya ....... G06N 5/022 |
| 2015/0257700 A1 * | 9/2015 | Fu ........................ A61B 5/7264 604/501 |

(Continued)

*Primary Examiner* — Van D Huynh
(74) *Attorney, Agent, or Firm* — Mintz Levin Cohn Ferris Glovsky and Popeo, P.C.

(57) ABSTRACT

A method may include applying, to a corpus of data, a first machine learning technique to identify candidate domains of an ontology mapping brain structure to mental function. The corpus of data may include textual data describing a plurality of mental functions and spatial data corresponding to a plurality of brain structures. A second machine technique may be applied to optimize a quantity of domains included in the ontology and/or a quantity of mental function terms included in each domain. The ontology may be applied to phenotype an electronic medical record and predict a clinical outcome for a patient associated with the electronic medical record. Related systems and articles of manufacture, including computer program products, are also provided.

18 Claims, 15 Drawing Sheets

(51) Int. Cl.
*G16H 30/40* (2018.01)
*G16H 10/60* (2018.01)
*G16H 50/30* (2018.01)
*G06N 5/04* (2006.01)
*G06K 9/62* (2022.01)
*G06N 3/02* (2006.01)
*G06V 10/70* (2022.01)

(52) U.S. Cl.
CPC .............. *G06N 5/042* (2013.01); *G06N 5/046* (2013.01); *G06V 10/768* (2022.01); *G16H 10/60* (2018.01); *G16H 30/40* (2018.01); *G16H 50/30* (2018.01)

(58) Field of Classification Search
CPC .... G06N 5/022; G06K 9/6223; G06K 9/6277; G06V 10/768; G16H 10/60; G16H 30/40; G16H 50/30; G16H 20/70; G16H 50/20
USPC .......................................................... 702/2
See application file for complete search history.

(56) References Cited

U.S. PATENT DOCUMENTS

| | | | |
|---|---|---|---|
| 2015/0294074 A1* | 10/2015 | Kawato | A61B 5/375 |
| | | | 702/19 |
| 2016/0235351 A1* | 8/2016 | Intrator | A61B 5/7264 |
| 2017/0042474 A1* | 2/2017 | Widge | A61N 1/36135 |
| 2017/0238879 A1* | 8/2017 | Ducreux | A61B 5/164 |
| 2018/0292902 A1* | 10/2018 | Min | A61B 5/375 |
| 2019/0090749 A1* | 3/2019 | Leuthardt | G06N 3/00 |
| 2020/0043615 A1* | 2/2020 | Reimann | A61B 5/4064 |
| 2020/0297210 A1* | 9/2020 | Gallacher | G16H 30/40 |

* cited by examiner

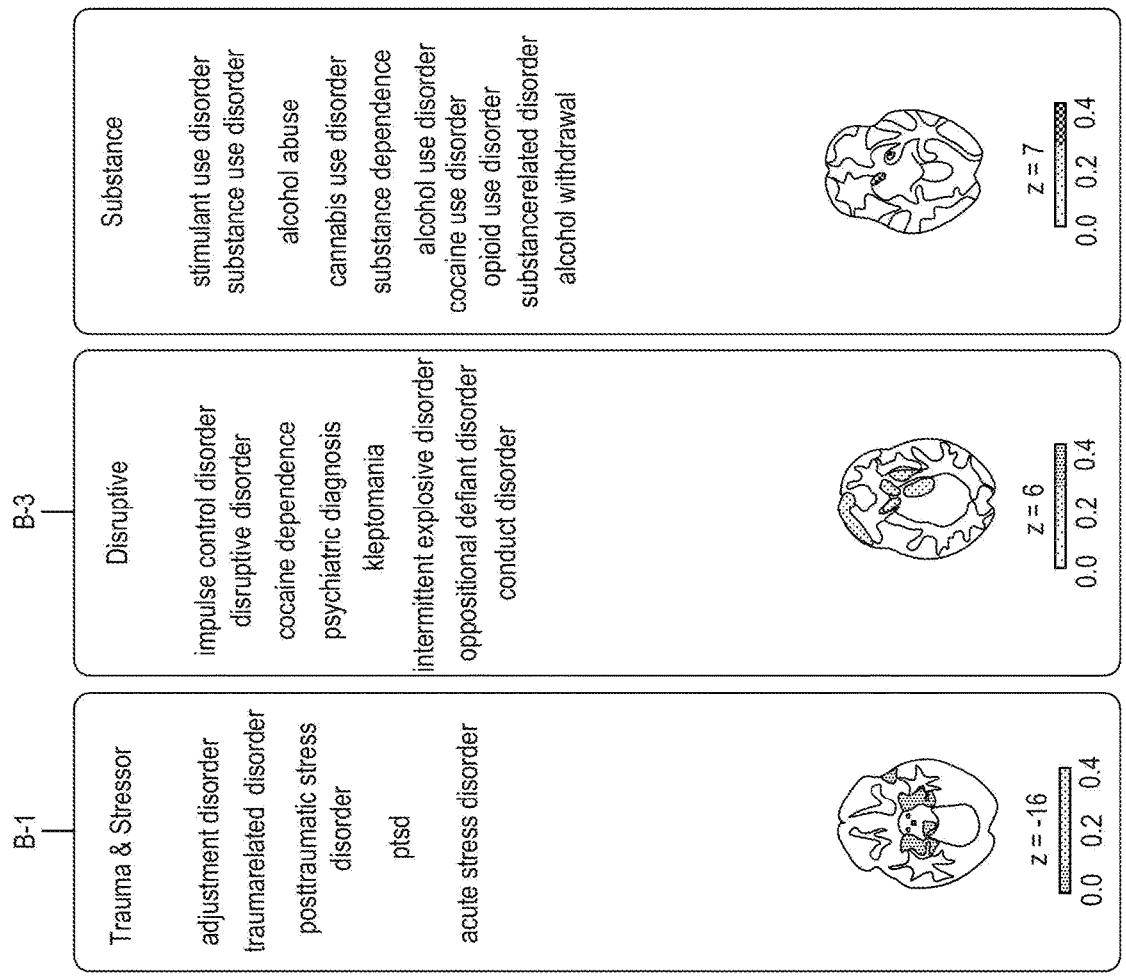
FIG. 4C - CONT'D

MACHINE LEARNING BASED GENERATION OF ONTOLOGY FOR STRUCTURAL AND FUNCTIONAL MAPPING

CROSS REFERENCE TO RELATED APPLICATION

This application claims priority to U.S. Provisional Application No. 62/853,958, filed on May 29, 2019 and entitled "NEUROIMAGING," the disclosure of which is incorporated herein by reference in its entirety.

This invention was made with Government support under contract MH116506 awarded by the National Institutes of Health. The Government has certain rights in the invention.

FIELD

The subject matter described herein relates generally to data processing and more specifically to the machine learning based generation of an ontology for structural and functional mapping.

BACKGROUND

Functional neuroimaging has been a longtime mainstay of human neuroscience. For example, functional neuroimaging may include applying one or more neuroimaging techniques to measure an aspect of brain function, with the goal of understanding the relationship between the activity across brain structures and mental functions. Examples of neuroimaging techniques include positron emission tomography (PET), functional magnetic resonance imaging (fMRI), electroencephalography (EEG), magnetoencephalography (MEG), functional near-infrared spectroscopy (fNIRS), and single-photon emission computed tomography (SPECT).

The neuroimaging imaging technique may be applied while a subject is performing a task such as, for example, being exposed to a visual stimulation. The neuroimaging technique may be applied in order to measure localized fluctuations in cerebral blood flow, electrical current, and/or magnetic fields that indicate activities in certain regions of the brain during the performance of the task. A link between the mental functions associated with the task and the brain structures responsible for the mental functions may be identified based on the regions shown to be active during the performance of the task. For example, activities in the occipital lobe of the brain when the subject is exposed to a visual stimulation may indicate a link between the occipital lobe and visual perception.

SUMMARY

In one aspect, there is provided a method for generating an ontology for structural and functional mapping. The method may include: applying, to a corpus of data, a first machine learning technique to identify one or more candidate domains of an ontology mapping brain structure to mental function, the corpus of data including textual data describing a plurality of mental functions and spatial data corresponding to a plurality of brain structures, and the ontology including a plurality of domains each of which (1) corresponding to a neural circuiting including one or more brain structures and including (2) one or more mental function terms associated with the one or more brain structures; applying a second machine technique to optimize a quantity of domains included in the ontology and/or a quantity of mental function terms included in each of the plurality of domains; and applying the ontology to process an electronic medical record.

In some variations, one or more features disclosed herein including the following features can optionally be included in any feasible combination. The first machine learning technique may include an unsupervised machine learning technique. The second machine learning technique may include a supervised machine learning technique.

In some variations, the first machine learning technique may include a k-means clustering algorithm configured to cluster the plurality of brain structures include in the corpus of data based at least on a co-occurrence value between each of the plurality of brain structures and each of the plurality of mental function terms. The co-occurrence value may correspond to a frequency at which a brain structure and a mental function term appear in a same article in the corpus of data. The co-occurrence value may be further weighted based on a pointwise mutual information (PMI) corresponding to a probability that the brain structure and the mental function term appear in the same article.

In some variations, the second machine learning technique may include a forward inference model trained to predict an occurrence of a brain structure based on an occurrence various quantities of mental function term. The second machine learning technique may further includes a reverse inference model trained to predict the occurrence of the various quantities of mental function terms based on the occurrence of a brain structure.

In some variations, an optimal quantity of domains in the ontology and/or an optimal quantity of mental function terms included in each of the plurality of domains may be selected to maximize a performance of the forward inference model and/or a performance of the reverse inference model. The performance of the forward inference model and/or the performance of the reverse inference model may include an average area under the receiver operating characteristic curve (ROC-AUC).

In some variations, the forward inference model and/or the reverse inference model may include a multilayer neural network classifier.

In some variations, the method may further include applying a natural language processing (NLP) technique to preprocess the corpus of data prior to applying the first machine learning technique, the preprocessing includes one or more of a case-folding, a removal of stop words and punctuation, and a lemmatization.

In some variations, the electronic medical record may be processed by at least determining, based at least on the ontology, one or more phenotypes associated with the electronic medical record and (2) predicting, based at least on the one or more phenotypes, a clinical outcome for a patient associated with the electronic medical record.

In some variations, the one or more phenotypes for the electronic medical record may be determined by at least determining, for each of the plurality of domains of the ontology, a rating corresponding to a proportion of mental function terms associated with the domain that is present in the electronic medical record. The one or more phenotypes may correspond to one or more highest rated domains and/or one or more domains having an above-threshold rating.

In some variations, the clinical outcome may include a duration of hospital stay, a quantity of office visits, a quantity of emergency room visits, healthcare cost, prescriptions, refills, comorbid conditions, and/or the like.

In some variations, the plurality of domains may include emotion, retrieval, language, arousal, and movement.

In another aspect, there is provided a system for generating an ontology for structural and functional mapping. The system may include at least one data processor and at least one memory storing instructions. When executed by the at least one data processor, the instructions may cause operations include: In some variations, one or more features disclosed herein including the following features can optionally be included in any feasible combination. The first machine learning technique may include an unsupervised machine learning technique. The second machine learning technique may include a supervised machine learning technique.

In some variations, the first machine learning technique may include a k-means clustering algorithm configured to cluster the plurality of brain structures include in the corpus of data based at least on a co-occurrence value between each of the plurality of brain structures and each of the plurality of mental function terms. The co-occurrence value may correspond to a frequency at which a brain structure and a mental function term appear in a same article in the corpus of data. The co-occurrence value may be further weighted based on a pointwise mutual information (PMI) corresponding to a probability that the brain structure and the mental function term appear in the same article.

In some variations, the second machine learning technique may include a forward inference model trained to predict an occurrence of a brain structure based on an occurrence various quantities of mental function term. The second machine learning technique may further includes a reverse inference model trained to predict the occurrence of the various quantities of mental function terms based on the occurrence of a brain structure.

In some variations, the electronic medical record may be processed by at least determining, based at least on the ontology, one or more phenotypes associated with the electronic medical record and (2) predicting, based at least on the one or more phenotypes, a clinical outcome for a patient associated with the electronic medical record.

In another aspect, there is provided a computer program product including a non-transitory computer-readable medium that stores instructions. When executed by at least one data processor, the instructions may cause operations that include: applying, to a corpus of data, a first machine learning technique to identify one or more candidate domains of an ontology mapping brain structure to mental function, the corpus of data including textual data describing a plurality of mental functions and spatial data corresponding to a plurality of brain structures, and the ontology including a plurality of domains each of which (1) corresponding to a neural circuiting including one or more brain structures and including (2) one or more mental function terms associated with the one or more brain structures; applying a second machine technique to optimize a quantity of domains included in the ontology and/or a quantity of mental function terms included in each of the plurality of domains; and applying the ontology to process an electronic medical record.

Implementations of the current subject matter can include, but are not limited to, methods consistent with the descriptions provided herein as well as articles that comprise a tangibly embodied machine-readable medium operable to cause one or more machines (e.g., computers, etc.) to result in operations implementing one or more of the described features. Similarly, computer systems are also described that may include one or more processors and one or more memories coupled to the one or more processors. A memory, which can include a non-transitory computer-readable or machine-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to generating an ontology for cerebral structural and functional mapping, it should be readily understood that such features are not intended to be limiting. The claims that follow this disclosure are intended to define the scope of the protected subject matter.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION OF THE INVENTION

Figure 1:
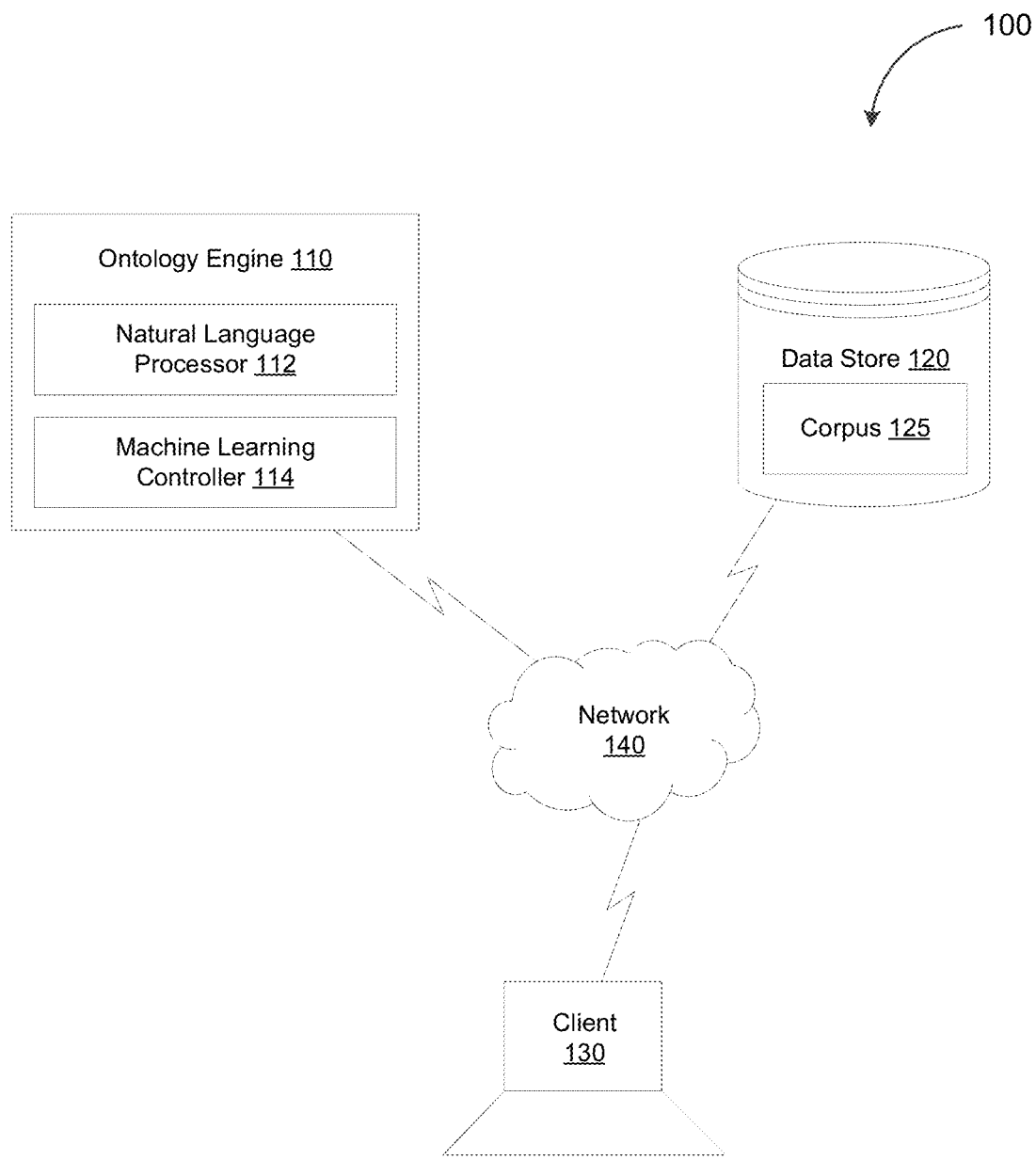
FIG. 1 depicts a system diagram illustrating an example of an ontology system, in accordance with some example embodiments.

Although functional neuroimaging aims to establish links between various structures of the brain and the corresponding functions, interpretation of the data obtained by applying neuroimaging techniques such as functional magnetic resonance imaging (fMRI) has traditionally occurred within conventional expert-determined knowledge frameworks. The unidirectional flow of inquiry starting from mental constructs defined decades earlier in psychology tends to amplify the subjective biases as well as reify theorized distinctions between psychological constructs instead of deriving new constructs anchored on brain function. The resulting links between brain structure and mental function may therefore have limited novelty and replicability.

In some example embodiments, an ontology mapping structures to functions may be generated by applying, to a corpus of data associated with an organ, one or more natural language processing (NLP) techniques and machine learning models. For example, one or more natural language processing (NLP) techniques and machine learning models may be applied to a corpus of data associated with the brain in order to generate an ontology mapping brain structures to the corresponding mental functions. The corpus of data associated with the brain may include a variety of articles associated with the brain, each of which including textual data describing one or more mental functions and/or spatial data corresponding to various brain structures. For example, the spatial data may include the coordinates of various neural circuits (e.g., populations of neurons interconnected by synapses), each of which corresponding to one or more brain structures. The resulting ontology may include one or more domains, each of which corresponding to a neural circuit having one or more brain structures. Accordingly, each domain in the ontology may map a set of brain structures (e.g., left amygdala) to one or more terms (e.g., "fear," "emotion," "memory," and/or the like) corresponding to the mental functions associated with the brain structures.

In some example embodiments, a natural language processing (NLP) technique may be applied to preprocess the corpus of data associated with the brain before extracting, from each article included in the corpus, textual data describing mental functions and spatial data corresponding to various neural circuits in the brain. The textual data describing mental functions and the spatial data corresponding to various neural circuits may be partitioned into a training set for generating the ontology and fitting models, a validation set for optimizing model hyperparameters and selecting thresholds for the ontology, and a testing set for comparing the ontology against other mappings between neural circuits and mental functions (e.g., Research Domain Criteria (RDoC), Diagnostic and Statistical Manual (DSM), and/or the like).

In some example embodiments, candidate domains for the ontology may be generated through an unsupervised learning approach that takes into account insights from information theory. For example, links between the terms describing mental functions and the corresponding brain structures may be established based on their co-occurrences across the training set. Co-occurrence values may be reweighted by pointwise mutual information (PMI) in order to emphasize correlation between brain structure and mental function instead of the frequency the corresponding textual data and/or structural data in the corpus. For instance, although the term "face identification task" may be infrequent in article texts and few coordinates are mapped to the left amygdala, their co-occurrence may nevertheless be associated with a high PMI value because they are both observed in the same small subset of articles.

The brain structures supporting distinctive sets of mental functions may then be defined by applying a clustering technique, such as k-means clustering, of the brain structures by their PMI-weighted co-occurrences with mental function terms, for example, over a range of k values (e.g., 2 to 25). Furthermore, the mental functions that are best representative of each brain structure may be identified in a manner that reflects prevalence rates across the corpus of data at least because PMI gives high weight to connections that are specific but not necessarily common. For example, none of the top 25 terms with the strongest PMI-weighted co-occurrence with the left amygdala are present in more than 0.2% of articles included in the corpus. The top mental function terms (e.g., the top 25 terms) for each brain structure may be identified based on associations across the training set, computed as point-biserial correlations between binary term occurrences and the centroid of occurrences across the brain structures that are present in each neural circuit. Accordingly, for the neural circuit containing the left amygdala, the most strongly associated terms were "fear", "emotion", and "memory," which respectively occurred in 10.82%, 18.12%, and 17.74% of the articles included in the corpus.

In some example embodiments, the number and size of domains in the ontology may be optimized by applying a supervised learning strategy. For example, while up to 25 terms may be initially assigned to a given neural circuit, fewer terms may suffice in representing its functional repertoire. In order to identify the set of terms and structures with the strongest predictive relationships, the optimal number of mental function terms per circuit may be determined based on how well term occurrences predicted and were predicted by occurrences of structures over a range of mental function terms (e.g., 5 to 25 mental function terms). For each neural circuit, a forward inference model (e.g., a multilayer neural network classifier) may be fit on the training set to predict the occurrence of brain structures based on the occurrence of various mental function terms. Furthermore, for each neural circuit, a reverse inference model (e.g., a multilayer neural network classifier) may be fit on the training set to predict the occurrence of mental function terms based on the occurrence of various brain structures.

The optimal number of mental function terms for each neural circuit may be selected to maximize validation set performance averaged between the forward inference model and the reverse inference model. Likewise, the optimal number of domains may be established by training the forward inference model and the reverse inference model over the range of k values used to cluster brain structures into the corresponding neural circuits. For example, the forward inference model may be trained to predict the occurrence of brain structures for various neural circuits while the reverse inference model may be trained to predict the occurrence of mental function terms in various optimized word lists. The forward inference model and the reverse inference model may be evaluated based on the validation set, with the performance metrics averaged between the forward inference model and the reverse inference models at each level of k. The resulting ontology may include 6 domains that corresponds to non-overlapping circuits spanning the brain. Moreover, each domain may be associated with mental constructs that include one or more mental function terms. The mental function term with the highest degree centrality of its term-term co-occurrences may be used to identify each domain.

FIG. 1 depicts a system diagram illustrating an example of an ontology system 100, in accordance with some example embodiments. Referring to FIG. 1, the ontology system 100 may include an ontology engine 110, a data store 120, and a client 130. The ontology engine 110, the data store 120, and the client 130 may be communicatively coupled via a network 140. The network 140 may be a wired network and/or a wireless network including, for example, a wide area network (WAN), a local area network (LAN), a virtual local area network (VLAN), a public land mobile network (PLMN), the Internet, and/or the like.

Referring again to FIG. 1, the ontology engine 110 may be configured to generate, based at least on a corpus 125 stored at the data store 120, a data-driven ontology mapping structures to functions. For example, the data-driven ontology include a plurality of domains, each of which corresponding to a neural circuit including one or more brain structures and including one or more terms corresponding to the mental function terms associated with the neural circuit. In some example embodiments, the ontology engine 110 may apply the data-driven ontology in order to phenotype an electronic medical record including textual data describing diagnoses, encounters, procedures, laboratory finding, and/or the like. For instance, the phenotypes for the electronic medical record may correspond to the domains included in the data-driven ontology that are determined to most align with the contents of the electronic medical record. These phenotypes may be used to predict a clinical outcome for a patient associated with the electronic medical record including, for example, a duration of hospital stay, a quantity of emergency room (ER) visits, a quantity of office visits, healthcare cost, prescriptions, refills, comorbid conditions, and/or the like.

Table 1 below provides some examples of brain structures. As noted, each domain in the data-driven ontology may correspond to a neural circuit. The examples of brain structures shown in Table 1 may form the various neural circuits included in the data-driven ontology.

TABLE 1

Left Frontal Pole
Left Insular Cortex
Left Superior Frontal Gyrus
Left Middle Frontal Gyrus
Left Inferior Frontal Gyrus, Pars Triangularis
Left Inferior Frontal Gyrus, Pars Opercularis
Left Precentral Gyrus
Left Temporal Pole
Left Anterior Superior Temporal Gyrus
Left Posterior Superior Temporal Gyrus
Left Anterior Middle Temporal Gyrus
Left Posterior Middle Temporal Gyrus
Left Temporo-Occipital Middle Temporal Gyrus
Left Anterior Inferior Temporal Gyrus
Left Posterior Inferior Temporal Gyrus
Left Temporo-Occipital Inferior Temporal Gyrus
Left Postcentral Gyrus
Left Superior Parietal Lobule
Left Anterior Supramarginal Gyrus TABLE 1-continued Left Posterior Supramarginal Gyrus
Left Angular Gyrus
Left Superolateral Occipital Cortex
Left Inferolateral Occipital Cortex
Left Intracalcarine Cortex
Left Frontal Medial Cortex
Left Supplementary Motor Cortex
Left Subcallosal Cortex
Left Paracingulate Gyrus
Left Anterior Cingulate
Left Posterior Cingulate
Left Precuneous
Left Cuneal Cortex
Left Frontal Orbital Cortex
Left Anterior Parahippocampus
Left Posterior Parahippocampus
Left Lingual Gyrus
Left Anterior Temporal Fusiform
Left Posterior Temporal Fusiform
Left Temporo-Occipital Fusiform
Left Occipital Fusiform
Left Frontal Operculum
Left Central Operculum
Left Parietal Operculum
Left Planum Polare
Left Heschl's Gyrus
Left Planum Temporale
Left Supracalcarine Cortex
Left Occipital Pole
Left Thalamus
Left Caudate
Left Putamen
Left Pallidum
Left Hippocampus
Left Amygdala
Left Accumbens
Left Brainstem
Left Cerebellum
Right Frontal Pole
Right Insular Cortex
Right Superior Frontal Gyrus
Right Middle Frontal Gyrus
Right Inferior Frontal Gyrus, Pars Triangularis
Right Inferior Frontal Gyrus, Pars Opercularis
Right Precentral Gyrus
Right Temporal Pole
Right Anterior Superior Temporal Gyrus
Right Posterior Superior Temporal Gyrus
Right Anterior Middle Temporal Gyrus
Right Posterior Middle Temporal Gyrus
Right Temporo-Occipital Middle Temporal Gyrus
Right Anterior Inferior Temporal Gyrus
Right Posterior Inferior Temporal Gyrus
Right Temporo-Occipital Inferior Temporal Gyrus
Right Postcentral Gyrus
Right Superior Parietal Lobule
Right Anterior Supramarginal Gyrus
Right Posterior Supramarginal Gyrus
Right Angular Gyrus
Right Superolateral Occipital Cortex
Right Inferolateral Occipital Cortex
Right Intracalcarine Cortex
Right Frontal Medial Cortex
Right Supplementary Motor Cortex
Right Subcallosal Cortex
Right Paracingulate Gyrus
Right Anterior Cingulate
Right Posterior Cingulate
Right Precuneous
Right Cuneal Cortex
Right Frontal Orbital Cortex
Right Anterior Parahippocampus
Right Posterior Parahippocampus
Right Lingual Gyrus
Right Anterior Temporal Fusiform
Right Posterior Temporal Fusiform
Right Temporo-Occipital Fusiform
Right Occipital Fusiform
Right Frontal Operculum
Right Central Operculum

TABLE 1-continued

Right Parietal Operculum
Right Planum Polare
Right Heschl's Gyrus
Right Planum Temporale
Right Supracalcarine Cortex
Right Occipital Pole
Right Thalamus
Right Caudate
Right Putamen
Right Pallidum
Right Hippocampus
Right Amygdala
Right Accumbens
Right Brainstem
Right Cerebellum Table 2 below provides some examples of mental functions that may be mapped to various brain structures by the data-driven ontology.

TABLE 2

2nd-Order Rule Acquisition
2-Stage Decision Task
3D Object
Abductive Reasoning
Abductive Reasoning Activity
Abductive Reasoning Function
Aberrant Behavior Checklist (Community)
Abstract Analogy
Bilingual Abstract Concrete Judgment
Abstract Concrete Task
Abstract Judgment Bilingual
Abstract Knowledge
Abstract Pattern
Abstract Task
Abstract-Concrete Judgment Bilingual
Abstract-Concrete Task
Acceleration Stimulus Transduction
Acoustic Coding
Acoustic Encoding
Acoustic Phonetic Processing
Acoustic Processing
Acquired Equivalence
Action
Action Imitation Task
Action Initiation
Action Observation Paradigm
Action Observation Task
Action Perception
Action-Perception Loop
Active Maintenance
Active Recall
Active Retrieval
Acuity
Acupuncture
Acupuncture Paradigm
Acupuncture Task
Adaptation
Adaptation Marshmallow Test
Adaptive Control
Adaptive N-Back Task
Addiction
Adolescent Symptom Inventory
Adult ADHD Clinical Diagnostic Scale
Adult ADHD Self-Report Scale
Adult Attachment Interview
Adult Behavior Checklist
Adult Penn Word Memory Test of Delayed Memory
Affect Perception
Affect Recognition
Affective Picture
Affective Representation
Affective Word
Agency
Agreeableness
Air Hunger
Alertness

TABLE 2-continued

Alexithymia
Alternating Run Paradigm
Altruism
Altruistic Motivation
Alveolar Sound
Ambiguous Figure Task
American National Adult Reading Test
Amodal Representation
Analog Representation
Analogical Encoding
Analogical Inference
Analogical Problem Solving
Analogical Reasoning
Analogical Reasoning Task
Analogical Transfer
Analogy
Anchoring
Anger
Angling Risk Task
Anhedonia
Animacy Decision
Animacy Perception
Animal Naming Task
ANT Task
Anticipation
Antisaccade Prosaccade Task
Antisaccade Task
Antisaccade-Prosaccade Task
Antisaccades
Antisaccades Paradigm
Antisocial Personality
Anxiety
Apparent Motion
Apparent Verticality Judgment
Apperception
Appetite
Appetitive Function
Appetitive Motivation
Arithmetic Processing
Arm
Arousal
Emotional Arousal
Physical Arousal
Articulation
Articulatory Loop
Articulatory Planning
Articulatory Rehearsal
Articulatory Suppression Task
Artificial Grammar Learning Task
Asian Character
Assimilation
Association
Association Learning
Associative Memory Encoding Task
Associative Priming
Ataxia
Attachment
Attending
Attended Channel
Attended Stimulus
Attending
Attention
Attention Bias
Attention Capacity
Attention Network Test
Attention Shift
Attention Shifting
Attention Span
Attention Switching Task
Attentional Bias
Attentional Blink
Attentional Blink Paradigm
Attentional Effort
Attentional Focusing
Attentional Resource
Attentional State
Attitude
Audio Narrative
Audiovisual Perception
Audiovisual Target Detection Task TABLE 2-continued Audition
Auditory Arithmetic Processing
Auditory Attention
Auditory Coding
Auditory Consciousness
Auditory Encoding
Auditory Feedback
Auditory Grouping
Auditory Imagery
Auditory Learning
Auditory Lexical Access
Auditory Localization
Auditory Masking
Auditory Masking Task
Auditory Memory
Auditory Modality
Auditory Perception
Auditory Recognition
Auditory Scene
Auditory Scene Analysis
Auditory Scene Perception
Auditory Sensation
Auditory Sentence Comprehension
Auditory Sentence Recognition
Auditory Stream Segregation
Auditory System Function
Auditory Temporal Discrimination Task
Auditory Tone Detection
Auditory Tone Discrimination
Auditory Tone Perception
Auditory Word Comprehension
Auditory Word Recognition
Auditory Working Memory
Autism Diagnostic Interview Revised
Autism Diagnostic Observation Schedule
Autism Spectrum Quotient
Autobiographical Memory
Autobiographical Memory Task
Autobiographical Recall
Automaticity
Autonoesis
Autonomic Nervous System Function
Availability Heuristic
Aversive Learning
AX-CPT Task
AX-DPX Task
Backward Chaining
Backward Digit Span Task
Backward Masking
Balance
Balloon Analogue Risk Task
Baroregulation
Barratt Impulsiveness Scale
Battelle Developmental Inventory
Becker-Degroot-Marschak Procedure
Becker-Degroot-Marschak Procedure
Becker-Degroot-Marschak Procedure
Beery-Buktenica Developmental Test of Visuomotor
Integration
Behavioral Activity
Behavioral Approach Inhibition System
Behavioral Approach System
Behavioral Approach/Inhibition System
Behavioral Inhibition
Behavioral Inhibition Cognitive
Behavioral Inhibition System
Behavioral Inhibition Temperament
Behavioral Investment Allocation Strategy
Behavioral Process
Behavioral Rating Inventory Executive Function
Behavioral System Function
Belief
Benton Facial Recognition Test
Bicarbonate Stimulus Transduction
Bickel Titrator
Big/Little Circle Task
Big Five Questionnaire
Big/Little Circle Task
Big/Little Circle Task
Bimanual Coordination Task TABLE 2-continued Binocular Convergence
Binocular Depth Cue
Binocular Disparity
Binocular Rivalry
Binocular Vision
Biological Motion Perception Paradigm
Biological Motion Perception Passive Viewing
Paradigm
Biological Motion Task
Birkbeck Reversible Sentence Comprehension Test
Birmingham Object Recognition Battery
Bistability
Bistable Percept Paradigm
Bitter Taste Sensation
Bitterness
Blindsight
Blink
Block Design Test
Block Tapping Test
Blocked Channel-Selection Task
Bodily Disposition
Bodily Process
Body Image Self-Reflection Task
Body Maintenance
Body Orientation
Body Representation
Border Ownership
Boston Naming Test
Braille Dot
Braille Reading
Braille Reading Paradigm
Braille Reading Task
Breathable Gas
Breathe Instruction
Breathe Response
Breathhold Instruction
Breathhold Response
Breathholding
Breathholding Paradigm
Brief Psychiatric Rating Scale
Brief Self Control Scale
Brief Symptom Inventory
Brixton Spatial Anticipation Test
Broad Autism Phenotype Questionnaire
Broader Phenotype Autism Symptom Scale
Button Press
Calculation
Calculation Paradigm
California Verbal Learning Test
California Verbal Learning Test II
Cambridge Face Memory Test
Cambridge Gambling Task
Cambridge Neuropsychological Test Automated
Battery
Cambridge Risk Task
Capability
Capability to Play Piano
Capability to Play Violin
Capability to Read
Capability to Read Music
Capability to Speak
Capability to Understand Language
Capacity Limitation
Capsaicin-Evoked Pain
Capture
Case Based Reasoning
CatBat Task
Categorical Clustering
Categorical Knowledge
Categorical Perception
Categorization
Categorization Task
Category Based Induction
Category Fluency Test
Category Learning
Cattell's Culture Fair Intelligence Test
Causal Inference
Center Epidemiologic Study Depression Scale
Central Attention
Central Coherence TABLE 2-continued Central Executive
Central Fixation
Centration
Change Blindness
Change Detection Task
Chapman Infrequency Scale
Chapman Magical Ideation Scale
Chapman Perceptual Aberration Scale
Chapman Physical Anhedonia Scale
Chapman Social Anhedonia Scale
Chemical Sensation
Chemical Stimulus Transduction
Chemonociception
Chewing
Chewing Paradigm
Chewing Swallowing Paradigm
Chewing Swallowing Paradigm
Chewing Swallowing Paradigm
Child Behavior Checklist
Children's Communication Checklist
Children's Memory Scale
Children's Psychiatric Rating Scale
Children's Yale-Brown Obsessive-Compulsive Scale
Chimeric Animal Stroop Task
Choice Reaction Time Task
Choice Task Risky Nonrisky Option
Chord Sequence
Chromatic Contrast
Chronesthesia
Chunk
Chunking
Ciliary Displacement Stimulus Transduction
Circadian Rhythm
Classical Conditioning
Classical Conditioning Paradigm
Classification Probe without Feedback
Click
Clinical Evaluation of Language Fundamentals 3
Clock Drawing Task
Cognition
Cognition
Cognitive Control
Cognitive Development
Cognitive Dissonance
Cognitive Effort
Cognitive Function
Cognitive Heuristic
Cognitive Load
Cognitive Map
Cognitive Process
Cognitive Reflection Test
Cognitive Representation
Cognitive State
Cognitive Training
Coherent Discourse Distinction Task
Coherent Incoherent Discourse Distinction Task
Coherent Motion
Coherent/Incoherent Discourse Distinction Task
Cold Pressor Test
Cold Sensation
Cold Stimulation
Color
Color Constancy
Color Naming Task
Color Perception
Color Recognition
Color Stroop
Color Trail Test
Color Discrimination Task
Color-Word Stroop Task
Color-Word Stroop Task Switching
Columbia Card Task
Communication
Communication Function
Communication Symbolic Behavior Scale Development Profile
Compensatory Tracking Task
Competition
Complex Span Test
Complex Trait Judgment Task
Comprehensive Test Phonological Processing
Concept
Concept Learning
Conceptual Category
Conceptual Coherence
Conceptual Metaphor
Conceptual Planning
Conceptual Priming
Conceptual Skill
Conceptualization
Bilingual Concrete Judgment
Concrete Task
Conditional Reasoning
Conditional Stop Signal Task
Conduct Disorder
Cone Confusion
Confidence Judgment
Conflict Adaptation Effect
Conflict Detection
Conjunction Search
Conjunction Search Task
Conners 3rd Edition
Conners Comprehensive Behavior Rating Scale
Connotation
Conscientiousness
Consciousness
Self-Consciousness
Consensus Decision Making Task
Consolidation
Constancy
Constituent Structure
Context
Context Dependence
Context Memory
Context Representation
Contextual Cueing Task
Contextual Knowledge
Contextual Semantic Priming Task
Contingency Learning
Continuous Performance Task
Continuous Performance Test (AX Version)
Continuous Recognition Paradigm
Continuous Tapping Task
Contour Integration Task
Contour Interpolation Task
Contrast Detection Task
Contrast Sensitivity Test
Contrastive Stress
Conventionality
Convergent Thinking
Conversation
Conversational Skill
Conversational Speech
Conversational Structure
Cooperation
Cooperativeness
Coordination
Coproduction
Copying Task
Coreference
Corpus Analysis
Corsi Block
Count
Counterconditioning
Counting
Counting Calculation
Counting Calculation Paradigm
Counting Paradigm
Counting Stroop
Counting Stroop Task
Counting Calculation
Covert
Covert Attention
Covert Naming Task
Covert Verb Generation Task
Creative Cognition
Creative Problem Solving
Creative Thinking
Criterion Task TABLE 2-continued Critical Period
Cross Modality
Cross-Modality
Crosstalk
Crowding
Crystallized Intelligence
Cue Approach Task
Cue Dependent Forgetting
Cue Validity
Cued Explicit
Cued Explicit Recognition
Cued Explicit Recognition Paradigm
Cueing
Cup Task
Curiosity
Cyberball Task
Dative Shift
Daydreaming
Decay Activation
Deception
Deception Task
Deception Task Paradigm
Decision
Decision Certainty
Decision Making
Decision Uncertainty
Declarative Knowledge
Declarative Memory
Declarative Rule
Deductive Inference
Deductive Reasoning
Deductive Reasoning Activity
Deductive Reasoning Function
Deductive Reasoning Paradigm
Deductive Reasoning Task
Deep Processing
Deep Structure
Defensive Aggression
Defiance
Delay Conditioning
Delay Discounting
Delay Discounting Task Paradigm
Delay Discounting Titration
Delay
Delayed Intention Task
Delayed Match Sample Paradigm
Delayed Match Sample Task
Delayed Memory Task
Delayed Non-Match Sample Paradigm
Delayed Nonmatch Sample Task
Delayed Recall Test
Delayed Response Task
Deliberation
Delusion
Depth Cue
Depth Perception
Desire
Detection
Detection
Gender Determination
Orientation Determination
Deterministic Classification
Deviance Detection
Devil Task
Dichotic Listening Task
Dickman Impulsivity Inventory
Dietary Decision Task
Difference Threshold
Differential Ability Scale
Digit
Digit Cancellation Task
Digit Coding Test
Digit Span Task
Digit Symbol Coding Test
Digit/Symbol Coding Test
Dimension Task
Diphthong
Direct Consciousness
Directed Forgetting Task
Discourse
Discourse Comprehension
Discourse Content Question
Discourse Content Test
Discourse Distinction Task
Discourse Knowledge
Discourse Planning
Discourse Processing
Discourse Production
Discriminate
Discrimination
Discrimination Activity
Discrimination Function
Disgust
Disposition
Distraction
Distraction Paradigm
Distraction Paradigm Capture
Distractor Attention Paradigm
Distributed Coding
Divergent Thinking
Divided Attention
Divided Auditory Task
Divided Auditory Attention
Divided Auditory Attention Paradigm
Domain Specificity
Door People Test
DOSPERT
Dot Motion Task
Dot Pattern Expectancy Task
Drawing
Drawing
Drawing Memory Task
Drawing Paradigm
Dream
Drinking
Drinking
Drinking Paradigm
Driving
DSM-IV
Dual Sensitization
Dual-Task Paradigm
Dual-Task Weather Prediction
Duckworth's Short Grit Scale
Dynamic Visual Perception
Dyslexia
Early Childhood Behavioral Questionnaire
Early Development Interview
Early Development Interview
Early Social Communication Scale
Eating
Eating/Drinking
Eating/Drinking Paradigm
Eating Paradigm
Eating Questionaire
Eating/Drinking
Echoic Memory
Echolocation
Echolocation Sensation
Eckblad and Chapman's Hypomanic Personality Scale
Economic Value Processing
Edge Detection
EDI
Edinburgh Handedness Inventory
Efficiency
Effort
Effort Valuation
Effortful Processing
Egocentric
Eidetic Memory
Elaborative Processing
Elaborative Rehearsal
Electric Stimulation
Electrical Sensation
Electrical Stimulation
Electroception Stimulus Transduction
Embedded Figure Test
Embodied Cognition
Emotion
Emotion Expression Identification TABLE 2-continued Emotion Induction
Emotion Perception
Emotion Processing fMRI Task Paradigm
Emotion Recognition
Emotion Recognition Task
Emotion Regulation
Emotion Regulation Questionnaire
Emotion Regulation Task
Emotional Body
Emotional Bonding
Emotional Decision Making
Emotional Enhancement
Emotional Expression
Emotional Face Recognition
Emotional Intelligence
Emotional Localizer fMRI Task Paradigm
Emotional Memory
Emotional Mimicry
Emotional Reappraisal
Emotional Regulation Task
Emotional Self-Evaluation
Emotional Stroop
Emotional Suppression
Empathy
Encoding
Encoding
Encoding Paradigm
Encoding Task
Episodic Buffer
Episodic Future Thinking
Episodic Intention
Episodic Learning
Episodic Memory
Episodic Planning
Episodic Prediction
Episodic Recall
Episodic Recall Paradigm
Episodic Recombination Paradigm
Episodic Simulation
Equilbrioception Sensation
Eriksen Flanker Task
Error Awareness Task
Error Detection
Error Signal
Error Trapping
Estimation
Excitation
Execution
Executive Function
Exogenous Attention
Expectancy
Expertise
Explicit Knowledge
Explicit Learning
Explicit Memory
Expressive One-Word Picture Vocabulary Test
Expressive Vocabulary Test
Extended Organism
Extension
Extension Paradigm
Externalizing
Extinction
Extradimensional Shift Task
Extraversion
Extrinsic Motivation
Eye
Eye Movement
Eye Puff
Eye Tracking Paradigm
Eysenck Personality Questionnaire
Face
Face Discrimination
Face Discrimination Paradigm
Face Identification Task
Face Maintenance
Face Matching Task
Face Monitor
Face Monitor Discrimination
Face Monitor Discrimination Paradigm
Face Monitor Paradigm
Face Monitor/Discrimination
Face N-Back Task
Face Perception
Face Recognition
Face Working Memory Task
Facial Age Recognition
Facial Attractiveness Recognition
Facial Expression
Facial Happiness Recognition
Facial Recognition
Facial Recognition Task
Facial Trustworthiness Recognition
Fagerstrom Test Nicotine Dependence
False Belief Task
False Font
False Memory
Fame Judgment Task
Familiarity
Fast Pain Sensation
Fatigue
Fear
Feature Comparison
Feature Detection
Feature Extraction
Feature Integration
Feature Search
Feature-Based Attention
Feedback
Feedback Processing
Feeding
Fictitious Event Ordering
Figurative Language
Figure Ground Reversal
Figure Ground Segregation
Figure Ground Task
Film Clip
Film Viewing
Film Viewing Paradigm
Filtering
Finger Tapping
Finger Tapping Paradigm
Finger Tapping Task
Fitts Task
Five Facet Mindfulness Questionnaire
Fixation
Fixation
Fixation Paradigm
Fixation Point
Fixation Task
Fixed Action Pattern
Flanker
Flanker Task Paradigm
Flashing Checkerboard
Flashing Checkerboard Paradigm
Flexion
Flexion Extension
Flexion Extension Paradigm
Flexion Paradigm
Flexion/Extension
Fluency Induction
Fluid Intelligence
Fluid-Coupled Ciliary Displacement Stimulus Transduction
Focus
Focused Attention
Following Command
Food
Foot
Foraging
Foreshortened View Task
Forgetting
Form Perception
Forward Digit Span Task
Fractal
Framing
Free List
Free Recall
Free Recall Function
Free Word List Recall
Free Word List Recall Paradigm

TABLE 2-continued

Frustration
Functional Fixedness
Functional Localizer fMRI Task
Future Time Perspective Questionnaire
Gambling
Gambling fMRI Task Paradigm
Gambling Task
Gastrointestinal
Gating
Gaze
Gender Discrimination Task
General Knowledge Task
Generalization
Generalization Instrumental Avoidance Task
Generating
Generative Memory Activity
Generative Verbal Activity
Generic Knowledge
Genitourinary System
Gestalt
Gestalt Grouping
Glasgow Coma Scale
Global Precedence
Global-Local Task
GM Paradigm
Go/No-Go
Go/No-Go Paradigm
Go/No-Go Task
Go Paradigm
Go Task
Goal
Goal Formation
Goal Maintenance
Goal Management
Goal Selection
Goal State
Go/No-Go
Go/No-Go Paradigm
Go/No-Go Task
Graded Naming Test
Grammatical Encoding
Grapheme
Graphemic Buffer
Grasping
Grasp Reflex
Grasping
Grasping Paradigm
Grasping Task
Gray Oral Reading Test 4
Grief
Guilt
Gustation
Gustation Processing
Gustatory Learning
Gustatory Memory
Gustatory Modality
Gustatory Perception
Gustatory Stimulation Liquid Flavor
Gustatory Stimulation Liquid Taste
Gustatory Stimulation Liquid Taste Flavor
Gustatory Stimulus Transduction
Gustatory System Function
Habit
Habit Learning
Habit Memory
Hallucination
Halstead-Reitan Battery
Hamilton Psychiatric Rating Scale Depression
Hand
Hand Chirality Recognition
Hand Side Recognition
Hand-Eye Coordination
Happiness
Haptic Illusion Task
Harm Avoidance
Hayling Sentence Completion Test
Hearing
Heartbeat
Heat
Heat Adaptation
Heat Sensation
Heat Sensitization
Heat Sensitization Adaptation
Heat Sensitization/Adaptation
Heat Stimulation
Hedonism
Heuristic Search
Hidden Path Learning Task
Hidden State Decision Making Task
Hierarchical Rule Task
High Energy Density Food Recognition
Higher Order Consciousness
Hill Climbing
Holt Laury Risk Titrator
Honesty
Hooper Visual Organization Test
Hopkins Symptom Checklist
Horizontal Checkerboard
Human Being
Humiliation
Humor
Hunger
Hungry Donkey Task
Hyperactivity
Hypercapnia
Hypomanic Personality Scale
17 Impulsiveness and Venturesomeness Questionnaire
Iconic Memory
Ideational Praxis Task
Identification
Illocutionary Force
Image Monitoring
Imageability
Imagery
Imagination
Imagining
Imagined Movement
Imagined Movement Paradigm
Imagined Object
Imagined Object Paradigm
Imagined Object Scene
Imagined Object Scene Paradigm
Imagined Objects/Scenes
Imagined Scene
Imagined Scene Paradigm
Immediate Memory Task
Immediate Recall Test
Implicit Association Task
Implicit Knowledge
Implicit Learning
Implicit Memory
Imprinting
Impulsiveness
Impulsivity
Inappropriate Speech
Inattention
Inattentional Blindness
Incentive Modulated Antisaccade Task
Incidental Encoding Task
Incidental Learning
Incubation
Indignation
Individual Body Part Movement
Induced Panic
Induction
Inductive Reasoning
Inductive Reasoning Activity
Inductive Reasoning Aptitude
Inductive Reasoning Function
Inference
Information Sampling Task
Infrared Laser
Infusion
Inhibition
Inhibition Return
Insight
Instinct
Instrumental Conditioning
Instrumental Learning
Instrumental Learning Task TABLE 2-continued Integration
Intelligence
Intensity Somatosensory Stimulation
Intention
Intentional Forgetting
Intentional Learning
Intentionality
Interdimensional/Extradimensional Shift Task
Interdimensional Shift Task
Interdimensional/Extradimensional Shift Task
Interference
Interference Control
Interference Resolution
Intermediate-Term Memory
Intermodal Preferential Looking Paradigm
Intermodal Selective Attention Task
Internal Speech
Internalizing
International Affective Picture System
Interoception
Interoceptive Modality
Interoceptive Representation
Interpersonal Behavior
Interpersonal Process
Interpretive Braille Reading
Interpretive Listening
Interpretive Verbal Activity
Interpretive Vision Based Reading
Interrogative
Intertemporal Choice
Intonation
Intradimensional Shift Task
Intrinsic Motivation
Introspection
Introversion
Involuntary Attention
Iowa Gambling Task
Irascibility
Irony
Irritability
Ishihara Plate Color Blindness
Isometric Force
Isometric Force Paradigm
Item Recognition Activity
Item Recognition Task
JND
Joint Attention
Joint Attention Non-Orienting Task
Joint Attention Social Nonsocial Orienting Task
Joint Social Nonsocial Orienting Task
Judging
Judgment
Judgment Line Orientation Task
Kanizsa Figure
Kaufman Brief Intelligence Test
Keep-Track Task
Kinaesthetic Representation
Kindness Priming
Kinesthesia
Kinesthetic Sensation
Kinesthetic System Function
Kirby Delay Discounting Task
Know Task
Knowledge
Landmark Task
Language
Language Acquisition
Language Comprehension
Language Learning
Language Perception
Language Problem Solving Behavior
Language Processing
Language Processing FMRI Task Paradigm
Language Production
Lateral Facilitation
Lateral Masking
Lateralized Activity
Learning
Left Finger Response Execution
Left Hand Response Execution
Left Toe Response Execution
Leg
Leiter International Performance Scale
Lemma
Length Match Task
Lethargy
Letter
Letter Case Judgment Task
Letter Comparison Task
Letter Fluency Test
Letter Matching Task
Letter Memory
Letter Naming Task
Letter N-Back Task
Letter Number Sequencing
Lexeme
Lexical Access
Lexical Ambiguity
Lexical Decision
Lexical Decision Task
Lexical Encoding
Lexical Processing
Lexical Retrieval
Lexicon
Libido
Life Satisfaction
Light Stimulus Transduction
Limited Capacity
Linguistic Capability
Linguistic Competence
Listening
Listening and Reading Task
Listening Span Task
Big/Little Circle Task
Living/Nonliving Judgment on Mirror-Reversed and Plain-Text Words
Living/Nonliving Judgment on Mirror-Reversed and Plain-Text Words
Living/Nonliving Judgment on Mirror-Reversed and Plain-Text Words
Living/Nonliving Task
Local Computation
Localization
Location Discrimination Paradigm
Locomotion
Locomotor Activity
Locomotor Function
Logic
Logical Reasoning
Logical Reasoning Task
Loneliness
Loneliness Rating Scale
Long-Term Memory
Loss
Loss Anticipation
Loss Aversion
Lying
MacArthur Communicative Development Inventory
Magnetic Field Stimulus Transduction
Magnetic Sensation
Magnitude Comparison
Maintenance
Manipulation
Manipulation
Manipulation Coherence Cohesion
Manipulation Individual Word
Manipulation ISI
Manipulation Language Nonverbal Behavior
Manipulation Predictability
Manipulation Predictability Acceptability
Manual Tracking
Match Sample
Match Sample Visual Search
Matching Familiar Figure Test
Matching Penny Game
Mathematical Problem Solving Behavior
Mathematical Reasoning
Maudsley Obsessive Compulsive Inventory
McGurk Effect TABLE 2-continued Meaning
Measured Emotion Differentiation Test
Mechanical Reasoning
Mechanical Stimulation
Mechanical Stimulus Transduction
Meditation
Meditation Task
Melody
Memory
Memory Acquisition
Memory Consolidation
Memory Decay
Memory Function
Memory Guided Saccade Task
Memory Process
Memory Recall
Memory Retention
Memory Retrieval
Memory Span Test
Memory Storage
Memory Trace
Memory-Driven Activity
Mental Arithmetic
Mental Arithmetic Task
Mental Calculation
Mental Capability
Mental Counting
Mental Disposition
Mental Imagery
Mental Imagery Task
Mental Process
Mental Representation
Mental Rotation
Mental Rotation Paradigm
Mental Rotation Task
Mentalizing Task
Metacognition
Metacognitive Skill
Metacomprehension
Metamemory
Metaphor
Meter
MicroCog Task
Micturition
Micturition
Micturition Task
Micturition Task Paradigm
Mindful Attention Awareness Scale
Mini Mental State Examination
Minimal Feature Match Task
Minnesota Multiphasic Personality Inventory
Mirror Reading Task
Mirror Tracing Task
Misattribution
Mixed Event-Related Probe
Mixed Gamble Task
Modified Erickson Scale Communication Attitude
Molecule Flow Stimulus Transduction
Monetary Incentive Delay Task
Monetary Reward Prediction Error
Monitor Discrimination
Monitoring
Montreal Cognitive Assessment
Mood
Moral Dilemma Task
Moral Reasoning Activity
Morphological Processing
Morphology
Morris Water Maze
Motion
Motion Aftereffect
Motion Detection
Motion Discrimination Task
Motion Processing
Motor Activity
Motor Control
Motor fMRI Task Paradigm
Motor Learning
Motor Planning
Motor Praxis TABLE 2-continued Motor Program
Motor Screening Task
Motor Selective Stop Signal Task
Motor Sequence Learning
Motor Sequencing Task
Motor System Function
Motorphotic Task
Mouse Tracking Paradigm
Mouth
Movement
Movement
Mullen Scale Early Learning
Muller-Lyer Illusion
Multiattribute Decision Making Task
Multiattribute Reward-Guided Decision Task
Multiclass N-Back Task
Multidimensional Personality Questionnaire
Multiobject Localizer Task
Multiplication Task
Multisensory
Multisensory Integration
Multisource Interference Task
Multistability
Multistable Perception
Multitasking
Musculoskeletal Equilibrium Sensation
Music
Music Comprehension
Music Comprehension Paradigm
Music Comprehension Production
Music Comprehension Production Paradigm
Music Comprehension/Production
Music Production
Music Production Paradigm
Musical Capability
Name
Naming
Naming Covert
Naming Covert Paradigm
Naming Overt
Naming Overt Paradigm
Naming Paradigm
Naming Task
Narrative
NART-R
National Adult Reading Test
Naturalistic Biological Motion
Naturalistic Scene
Navigation
Navigation Task
N-Back
N-Back Paradigm
N-Back Task
Negative Emotion
Negative Feedback Processing
Negative Priming
Negative Priming Task
Neologism
Nervous System Function
Network Traversal Task
Neuroplasticity
Neuroticism
NIH Toolbox 2-Minute Walk Endurance Test
NIH Toolbox 4-Meter Walk Gait Speed Test
NIH Toolbox 9-Hole Pegboard Dexterity Test
NIH Toolbox Dimensional Change Card Sort Test
NIH Toolbox Dynamic Visual Acuity Test
NIH Toolbox General Life Satisfaction Survey
NIH Toolbox Grip Strength Test
NIH Toolbox Hearing Handicap Inventory
NIH Toolbox Hearing Threshold Test
NIH Toolbox List Sorting Working Memory Test
NIH Toolbox Meaning Purpose Survey
NIH Toolbox Odor Identification Test
NIH Toolbox Oral Reading Recognition Test
NIH Toolbox Oral Symbol Digit Test
NIH Toolbox Pain Intensity Survey
NIH Toolbox Pain Interference Survey
NIH Toolbox Picture Sequence Memory Test
NIH Toolbox Picture Vocabulary Test

TABLE 2-continued

NIH Toolbox Positive Affect Survey
NIH Toolbox Standing Balance Test
NIH Toolbox Taste Intensity Test
NIH Toolbox Vision-Related Quality Life Survey
NIH Toolbox Visual Acuity Test
NIH Toolbox Words-in-Noise Test
Nine-Hole Peg Test
No Task
No Paradigm
No Task
Nociception
Noesis
Noise
Noise Sensitivity
Nonjudgment Mirror-Reversed Plain-Text Word
Nonchoice Task
Nondeclarative Knowledge
Nondeclarative Memory
Noninstrumental Information Seeking Task
Nonpainful Electrical Stimulation
Nonpainful Electrical Stimulation Paradigm
Nonpainful Thermal Stimulation
Nonpainful Thermal Stimulation Paradigm
Nonspatial Cuing Paradigm
Nontarget
Nonverbal Vocal Sound
Nonvocal Sound
Nonword Language Localizer
Nonword Repetition Task
Novelty Detection
Novelty Detection Task
Novelty Seeking
NPU-Threat Test
Numerical Comparison
Numerical Scale Judgment
Numerical Working Memory Task
Numerosity Estimation Task
Nutrition Function
Object Alternation Task
Object Categorization
Object Centered Representation
Object Classification
Object Decision Task
Object Detection
Object Discrimination
Object Maintenance
Object Manipulation
Object Naming Task
Object N-Back
Object One-Back Task
Object Perception
Object Perception Task
Object Rating Task
Object Recognition
Object Recognition Task
Object Working Memory Task
Object-Based Attention
Object Discrimination Task
Observation
Obsession
Oculomotor Delayed Response
Oculomotor Function
Oddball Detection
Oddball Discrimination
Oddball Discrimination Paradigm
Oddball Task
Odd/Even Task
Odor
Offensive Aggression
Olfaction
Olfactory Consciousness
Olfactory Discrimination
Olfactory Discrimination Paradigm
Olfactory Modality
Olfactory Monitor
Olfactory Monitor Discrimination Paradigm
Olfactory Monitor Paradigm
Olfactory Monitoring
Olfactory Monitoring/Discrimination
Olfactory Perception
Olfactory Sensation
Olfactory Stimulus Transduction
One Touch Stockings of Cambridge
Openness
Openness to Experience
Operant Task
Operation Span Task
Optical Illusion
Orgasm
Orientation Match Task
Orientation Test
Orthographic Discrimination
Orthographic Discrimination Paradigm
Orthographic Lexicon
Orthographic Task
Orthography
Osmoregulation
Overlapping Figure Task
Overt
Overt Attention
Overt Naming
Overt Word Repetition
Paced Auditory Serial Addition Test
Pain
Pain Discrimination
Pain Discrimination Paradigm
Pain Discrimination Task
Pain Habituation
Pain Monitor
Pain Monitor Discrimination Paradigm
Pain Monitor Discrimination Task
Pain Monitor Paradigm
Pain Monitor Task
Pain Monitor/Discrimination Task
Pain Sensation
Pain Sensitization
Painful Stimulation
Paired Associate
Paired Associate Learning
Paired Associate Recall
Paired Associate Recall Paradigm
Pantomime Task
Parallel Search
Parallel Serial Search
Parallel/Serial Search
Paranoia
Paraphasia
Parasympathetic Nervous System Function
Parity Judgment Task
Parrott Scale
Parsing
Partial Report Procedure
Passive Attention
Passive Avoidance Task
Passive Listening
Passive Listening Paradigm
Passive Viewing
Passive Viewing Paradigm
Past Tense
Pattern Comparison Task
Pattern Maintenance
Pattern Recognition
Pavlovian Conditioning
Pavlovian Conditioning Task
PDD Behavior Inventory
Peabody Picture Vocabulary Test
PEBL Perceptual Vigilance Task
Pelvis
Penn Conditional Exclusion Test
Penn Continuous Performance Task
Penn Emotion Recognition Task
Penn Face Memory Test
Penn Facial Memory Test Delayed Memory
Penn Fractal N-Back
Penn Matrix Reasoning Test
Penn Motor Praxis
Penn Visual Object Learning Test
Penn Visual Object Learning Test Delayed Memory
Penn Vocabulary Test TABLE 2-continued Penn Word Memory Test
Penn's Logical Reasoning Test
Perception
Perceptual Binding
Perceptual Categorization
Perceptual Closure Task
Perceptual Discrimination Task
Perceptual Fluency
Perceptual Identification
Perceptual Learning
Perceptual Organization
Perceptual Priming
Perceptual Similarity
Perceptual Skill
Perfectionism
Performance Monitoring
Perseveration
Persistence
Personality
Personality Trait
Phasic Pain Stimulation
Phonation
Phoneme Detection Task
Phonemic Fluency Task
Phonemic Paraphasia
Phonetic Discrimination Task
Phonetics
Phonological Assembly
Phonological Awareness
Phonological Buffer
Phonological Code
Phonological Comparison
Phonological Discrimination
Phonological Discrimination Paradigm
Phonological Encoding
Phonological Loop
Phonological Processing
Phonological Retrieval
Phonological Task
Phonological Working Memory
Phonology
Photo Sensation
Phototransduction
Physical
Piaget's Water Jar Task
Picture
Picture Naming Task
Picture/Word Stroop Test
Pitch Discrimination
Pitch Discrimination Paradigm
Pitch Monitor
Pitch Monitor Discrimination
Pitch Monitor Discrimination Paradigm
Pitch Monitor Paradigm
Pittsburgh Sleep Quality Index
Place Maintenance
Planning
Play Activity
Plus/Minus
Point
Point Light
Pointing
Pointing Paradigm
Porteus Maze Test
Position Gap Match Task
Positive Feedback Processing
Positive and Negative Affect Scale
Positive Priming
Posner Cueing Task
Posner Task Paradigm
Potential Monetary Loss
Potential Monetary Reward
Pragmatic Inference
Pragmatic Knowledge
Pragmatic Reasoning
Preattentive Processing
Preconscious Perception
Predictive-Inference Helicopter Task
Preference
Prejudice
Preparation
Preschool Language Scale
Pressure Stimulus Transduction
Primary Memory
Priming
Proactive Control
Proactive Interference
Probabilistic Classification Task
Probabilistic Gambling Task
Probabilistic Reversal Learning Task
Probabilistic Selection Task
Problem Solving
Problem Solving Task
Procedural Knowledge
Procedural Learning
Procedural Memory
Procedural Rule
Processing Capacity
Processing Speed
Processing Stage
Production Nonfacial Communication
Productive Facial Communication
Pronunciation
Proper Noun
Proprioception
Proprioceptive System Function
Prosaccade Task
Prosodic Stress
Prosody
Prospection
Prospective Memory
Prospective Memory Task
Prospective Planning
Prototype
Prototype Distortion Task
PRP
Pseudoword Naming Task
Pseudowords
Psychological Refractory Period
Psychological Refractory Period Paradigm
Psychological Refractory Period Paradigm
Psychophysics Task
Psychosis
Punishment Processing
Pursuit Rotor
Pursuit Rotor Task
Pursuit Tracking Task
Pyramid Palm Tree Task
Quantitative Skill
Random Dot
Random Number Generation Task
Rapid Automatized Naming Test
Rapid Serial Object Transformation
Rapid Serial Visual Presentation Task
Rapid Visual Information Processing
Raven Advanced Progressive Matrix
Reaction Time
Read
Reading
Covert Reading
Reading (Covert) Paradigm
Overt Reading
Reading (Overt) Paradigm
Reading Paradigm
Reading Span Task
Reappraisal Task
Reasoning
Reasoning Activity
Reasoning Function
Recall
Recall Test
Recency Judgment Task
Reception Facial Communication
Reception Nonfacial Communication
Reciprocal Artwork Evaluation Task
Recitation
Recitation Covert
Recitation Covert Paradigm
Recitation Overt
Recitation Overt Paradigm TABLE 2-continued Recitation Repetition Covert
Recitation Repetition Covert Paradigm
Recitation Repetition Overt
Recitation Repetition Overt Paradigm
Recitation Repetition Paradigm
Recitation/Repetition
Recitation/Repetition (Covert)
Recitation/Repetition (Overt)
Recognition
Recognition Memory
Recognition Memory Function
Recognition Memory Test
Reconsolidation
Reentrant Processing
Regret
Regularity Change Detection
Regulated Heat Stimulation
Rehearsal
Rehearsal Loop
Reinforcement Learning
Reinstatement
Relational Comparison
Relational Learning
Relational Processing fMRI Task Paradigm
Relational Reasoning Task
Remember Know Task
Remember Task
Remembering
Remember/Know Task
Remote Associate Test
Remote Memory
Repeat
Repetition
Covert Repetition
Repetition (Covert) Paradigm
Overt Repetition
Repetition (Overt) Paradigm
Repetition Priming
Representation
Repressed Memory
Requested Recall
Requested Recall Function
Resistance Distractor Inference
Resource
Resource Limit
Resource Sharing
Respiration
Response Bias
Response Conflict
Response Execution
Response Inhibition
Response Mapping Task
Response Priming
Response Selection
Rest
Rest (Eyes Closed)
Rest (Eyes Open)
Rest Paradigm
Restricted Behavior
Retention
Retinotopic Mapping Task
Retinotopic Representation
Retrieval
Retrieval Cue
Retrieval-Induced Forgetting Task
Retroactive Interference
Reversal Learning Task
Reversal Weather Prediction
Reversed Speech
Reward
Reward Anticipation
Reward Dependence
Reward Learning
Reward Processing
Reward Task Paradigm
Reward Valuation
Rey Auditory Verbal Learning Task
Reynell Developmental Language Scale
Rey-Ostereith Complex Figure Test
Rhyme Verification Task TABLE 2-continued Rhythm
Right Finger Response Execution
Right Hand Response Execution
Right Toe Response Execution
Rigidity
Risk
Risk Aversion
Risk Processing
Risk Seeking
Risky Gain Task
Rivermead Behavioural Memory Test
Route Knowledge
Route Learning
Routine
Roving Somatosensory Oddball Task
Rubber Hand Illusion
Rule
Rule Learning
Running Memory
Saccade
Saccade Paradigm
Saccadic Eye Movement
Sadness
Salience
Salthouse and Babcock Listening Span Task
Salty Taste Sensation
Same-Different Task
Satiety
Scale for the Assessment of Negative Symptoms
Scale for the Assessment of Positive Symptoms
Scene Recognition Task
Schema
Search
Seeing
Selection-Optimization-Compensation Questionnaire
Selection-Optimization-Compensation Questionnaire
Selective Attention
Selective Attention Task
Selective Control
Self-Control
Self-Knowledge
Self-Monitoring
Self-Monitoring Task
Self-Ordered Pointing Task
Self-Regulation Questionnaire
Self-Talk
Self-Directedness
Self-Esteem
Self-Reflection
Self-Transcendence
Semantic Anomaly Judgment Task
Semantic Association Task
Semantic Categorization
Semantic Category
Semantic Classification Task
Semantic Decision Task
Semantic Discrimination
Semantic Discrimination Paradigm
Semantic Fluency Task
Semantic Information
Semantic Knowledge
Semantic Memory
Semantic Memory Task
Semantic Monitor
Semantic Monitor Discrimination Paradigm
Semantic Monitor Paradigm
Semantic Network
Semantic Priming
Semantic Processing
Semantic Relatedness Task
Semantic Task
Semantic Working Memory
Semantics
Sensation-Seeking
Sense of Body Ownership
Sense of Ownership
Sensitivity Change
Sensory Defensiveness
Sensory Memory
Sensory Perception TABLE 2-continued Sensory Profile
Sensory Stimulus Transduction
Sensory System Function
Sentence Completion Test
Sentence Comprehension
Sentence Content Test
Sentence Discourse Content Test
Sentence Language Localizer
Sentence Nonword Language Localizer
Sentence Processing
Sentence Production
Sentence Recognition
Sentence/Discourse Content Test
Sentence/Nonword Language Localizer
Sentence/Picture Matching Task
Sequence Encoding
Sequence Learning
Sequence Learning Paradigm
Sequence Recall
Sequence Recall Learning
Sequence Recall Learning Paradigm
Sequence Recall Paradigm
Sequence Recall/Learning
Sequence Reproduction
Sequential Shape Matching
Serial Learning
Serial Processing
Serial Reaction Time Task
Serial Search
Set Shifting
Set Shifting Task
Sexual Arousal
Sexual Gratification
Sexuality
Shadowing Task
Shallow Processing
Shame
Shape
Shape Recognition
Shift Task
Short Penn Continuous Performance Test-Number Letter Version
Short-Term Memory
Short-Term Memory Task
Shoulder
Simon Task
Simon Task Paradigm
Simple Reaction Time Task
Simple Span Task
Singing
Single Item Food Choice Task
Single Task Weather Prediction
Size Match Task
Skeletomotor Reflex Activity
Skeletomotor Reflex Function
Skepticism
Skill
Skill Acquisition
Sleep
Sleep Paradigm
Slow Pain Sensation
Smelling
Smile Instruction
Smile Response
Smoking
SOC
Social Bargaining fMRI Task
Social Cognition
Social Cognition fMRI Task Paradigm
Social Cognition (Theory of Mind) fMRI Task Paradigm
Social Communication Questionnaire
Social Competence Questionnaire
Social Context
Social Inference
Social Influence Emotion Task
Social Influence Food Preference Task
Social Intelligence
Social Judgment Face Task
Social Judgment Task
Social Localizer fMRI Task Paradigm
Social Motivation
Social Norm Processing
Social Norm Processing Task
Social Phobia
Social Responsiveness Scale
Solid Object-Coupled Ciliary Displacement Stimulus Transduction
Somatic
Somatic Sensation
Somatosensation
Somatosensory System Function
Somesthesis
Sound Perception
Sound Sensation
Sour Taste Sensation
Source Memory
Source Memory Test
Source Monitoring
Space Fortress
Space Fortress Oddball
Span/Supra-Span Test
Span Test
Span/Supra-Span Test
Spatial
Spatial Ability
Spatial Attention
Spatial Cognition
Spatial Cuing Paradigm
Spatial Delayed Response Task
Spatial Discrimination
Spatial Discrimination Paradigm
Spatial Localization
Spatial Localizer fMRI Task Paradigm
Spatial Location
Spatial Location Discrimination
Spatial Location Discrimination Paradigm
Spatial Location/Discrimination
Spatial Memory
Spatial N-Back Task
Spatial Recognition Memory
Spatial Selective Attention
Spatial Span Test
Spatial Working Memory
Spatial Working Memory Localizer Task
Spatial Working Memory Task
Speech
Speech Detection
Speech Perception
Speech Processing
Speech Production
Spelling Task
Spielberger's State-Trait Anxiety Questionnaire
Spontaneous Recovery
Spreading Activation
Standard Localizer fMRI Task Paradigm
Stanford Leisure-Time Activity Categorical Item
Stanford-Binet Intelligence Scale
Stereopsis
Stereotype
Sternberg Delayed Recognition Task
Sternberg Directed Forgetting
Sternberg Item Recognition Task
Sternberg Recent Probe
Sternberg Task Paradigm
Stimulus Detection
Stimulus Selective Stop Signal Task
Stocking Cambridge Task
Stop Signal Task
Stop Signal Task Dot Motion Discrimination
Stop Signal Task Letter Naming
Stop Signal Task Pseudo Word Naming
Stop Signal Walking Task Stroop
Stop-Change Task
Story Comprehension
Strategy
Strength
Stress
String Maintenance
Stroop TABLE 2-continued Stroop Task
Stroop Task Paradigm
Structured Clinical Interview for Diagnostic Statistical Manual Mental Disorder
Structured Clinical Interview for Diagnostic Statistical Manual Mental Disorder (DSM-IV)
Subconscious
Subjective Emotional Picture Discrimination
Subjective Emotional Picture Discrimination Paradigm
Subjective Food Value
Subjective Value Judgment
Sublexical Route
Subliminal Perception
Suicidal Ideation
Supervisory Attentional System
Supra Test
Surface Dyslexia
Surface Property Object Paradigm
Surprise
Sustained Attention
Sustained Attention Response Task
Swallow
Swallowing
Swallowing Paradigm
Sweet Taste Sensation
Syllable
Symbol
Symbol Coding Test
Symbol Counter Task
Symbol/Digit Substitution
Sympathetic Nervous System Function
Symptom Checklist 90 Revised
Synchrony Judgment Task
Synchrony Perception
Syntactic Acceptability Judgement Task
Syntactic Discrimination
Syntactic Discrimination Paradigm
Syntactic Parsing
Syntactic Processing
Syntactic Task
Syntacting Semantic fMRI Task Paradigm
Syntax
Tactile Consciousness
Tactile Discrimination
Tactile Discrimination Paradigm
Tactile Modality
Tactile Monitor
Tactile Monitor/Discrimination
Tactile Monitor/Discrimination Paradigm
Tactile Monitor Paradigm
Tactile Monitor/Discrimination
Tactile Stimulation
Tactile Working Memory
Tapping Task
Target
Target Detection Task
Task Difficulty
Task Set
Task Switching
Task Switching 3x2
Task Switching Paradigm
Task Switching
Taste
Taste Aversion
Taste Sensation
Tasting
Temperament
Temperament Character Inventory
Temperature Sensation
Temperature Stimulus Transduction
Temporal Cognition
Temporal Discounting Task
Temporal Order Judgment Task
Ten Item Personality Questionnaire
Test Adolescent Adult Language
Test Early Language Development
Test Language Development
Test Term
Test Variable Attention
Test Word Reading Efficiency
Text Comprehension
Text Processing
Theory of Mind
Theory of Mind Task
Theory of Mind Task Paradigm
Theories of Willpower Scale
Thermal Grill Illusion
Thermoregulation
Thermosensation
Think/No-Think Task
Think Task
Thinking
Thinking Language
Think/No-Think Task
Thirst
Thirst Induction
Thought
Time Wall
Time-Series of Response Time
TMS
Tobacco Craving Questionnaire
Tone
Tone Counting
Tone Detection
JND Tone Detection
Tone Discrimination
Tone Discrimination Paradigm
Tone Matching
Tone Monitor
Tone Monitor Discrimination
Tone Monitor Discrimination Paradigm
Tone Monitor Paradigm
Tone Monitor/Discrimination
Tone Recognition
Tongue Response Execution
Tonic Pain Stimulation
Tool Maintenance
Top Processing
Topographical Memory
Torso
Touch Sensation
Touch Stimulus Transduction
Touching
Tower of Hanoi
Tower of London
Tower of London Imagine
Tower of London Paradigm
Trace Conditioning
Track
Trail Making Test B
Trait Anxiety
Transcranial Magnetic Stimulation Paradigm
Transduction
Transitive Inference Task
Trauma Recall
Traumatic Memory
Treatment Self-Regulation Questionnaire
Two Item Food Choice Task
Ultimatum Game
Ultimatum Game
Ultimatum Game
Umami Taste Sensation
Uncertainty
Unconscious Perception
Unconscious Process
Underlining Test
Understanding Mental State
Unified Parkinson Disease Rating Scale
Unisensory
Updating
Updating Task
UPPS-P Impulsivity Scale
Utility
Uznadze Haptic Illusion Task
Valence
Vandenberg Kuse Task
Vection
Verb Generation Task
Verbal Activity
Verbal Description Visual Depiction TABLE 2-continued Verbal Fluency
Verbal Fluency Task
Verbal Function
Verbal Memory
Verbal Speaking
Verbal Working Memory Task
Verbal Writing
Vernier Discrimination Task
Vertical Checkerboard
Vestibular System
Vestibular Control
Vestibular Stimulation
Vestibular System Function
Vibratory Stimulation
Vibrotactile Discrimination
Vibrotactile Discrimination Paradigm
Vibrotactile Monitor
Vibrotactile Monitor Discrimination
Vibrotactile Monitor Discrimination Paradigm
Vibrotactile Monitor Paradigm
Vibrotactile Monitor/Discrimination
Video Game
Video Game Paradigm
Vigilance
Vineland Adaptive Behavior Scale
Visceral Sensation
Vision
Visual Acuity
Visual Alignment Task
Visual Analogue Scale
Visual Angle
Visual Attention
Visual Attention Paradigm
Visual Attention Task
Visual Awareness
Visual Body Recognition
Visual Buffer
Visual Color Discrimination
Visual Consciousness
Visual Distractor Visual Attention Paradigm
Visual Face Recognition
Visual Form Discrimination
Visual Form Recognition
Visual Illusion Susceptibility
Visual Imagery
Visual Letter Recognition
Visual Localization
Visual Masking
Visual Memory
Visual Modality
Visual Motion
Visual Number Recognition
Visual Object
Visual Object Detection
Visual Object Learning Test
Visual Object Maintenance
Visual Object Recognition
Visual Orientation
Visual Pattern Recognition
Visual Pattern Test
Visual Perception
Visual Place Recognition
Visual Problem Solving Behavior
Visual Pseudoword Recognition
Visual Pursuit
Visual Pursuit Paradigm
Visual Pursuit Tracking
Visual Pursuit Tracking Paradigm
Visual Pursuit/Tracking
Visual Recognition
Visual Representation
Visual Search
Visual Search Task
Visual Sensation
Visual Sentence Recognition
Visual String Recognition
Visual System Function
Visual Tool Recognition
Visual Tracking
Visual Tracking Paradigm
Visual Word Recognition
Visual Working Memory
Visual World Paradigm
Visually Guided Saccade Task
Visuospatial Attention
Visuospatial Cueing Task
Visuospatial Sketch Pad
Vocal Response Execution
Voice Perception
Volatile Bandit
WAIS Arithmetic
WAIS Comprehension
WAIS Digit Span
WAIS Object Assembly
WAIS Picture Arrangement
WAIS Picture Completion
WAIS Similarity
WAIS Vocabulary
WAIS information
Wanting
Warrington's Face Recognition Test
Warrington's Face/Word Recognition Test
Warrington's Face/Word Recognition Test
Warrington's Word Recognition Test
Wason Card Selection Task
Wechsler Abbreviated Scale Intelligence
Wechsler Adult Intelligence Scale Revised
Wechsler Adult Intelligence Scale-Revised
Wechsler Intelligence Scale Child Revised
Wechsler Memory Scale Fourth Edition
Whistle
Whistling
Whistling Paradigm
Why/How Task
Willingness Wait Task
Wisconsin Card Sorting Test
Wisconsin Card Sorting Test Paradigm
WISC-R Maze
Wisdom
Word
Word Attack
Word Comprehension
Word Comprehension Task
Word Fluency Test
Word Generation
Word Generation (Covert) Paradigm
Word Generation (Overt) Paradigm
Word Generation Paradigm
Word Generation Task
Word Identification
Word Imageability
Word Maintenance
Word One-Back Task
Word Order
Word Pronunciation
Word Recall
Word Recognition
Word Recognition Task
Word Repetition
Word Stem Completion
Word Stem Completion (Covert)
Word Stem Completion (Covert) Paradigm
Word Stem Completion (Overt)
Word Stem Completion (Overt) Paradigm
Word Stem Completion Paradigm
Word-Picture Matching Task
Word-Picture Verification Task
Working Memory
Working Memory fMRI Task Paradigm
Working Memory Function
Working Memory Maintenance
Working Memory Retrieval
Working Memory Storage
Working Memory Updating
WRAT-4 Math Computation
WRAT-4 Word Reading
Writing
Writing
Writing Paradigm
Writing Task TABLE 2-continued Yellow Light Game
Young Mania Rating Scale
Zimbardo Time Perspective Inventory
Zoo Map Test
Zuckerman Sensation Seeking Scale The corpus 125 may include a plurality of articles associated with the brain (e.g., human and/or nonhuman brain), each of which including textual data describing one or more mental functions and/or spatial data corresponding to various brain structures. A data-driven ontology mapping brain structures to mental functions may be generated by applying one or more natural language processing (NLP) techniques and machine learning models. Accordingly, as shown in FIG. 1, the ontology engine 110 may include a natural language processor 112 and a machine learning controller 114.

In some example embodiments, the natural language processor 112 may be configured to preprocess each of the articles included in the corpus 125. The processing may include case-folding, removal of stop words and punctuation, lemmatization (e.g., with WordNet), and/or the like. The preprocessed articles from the corpus 125, which includes textual data describing mental functions as well the spatial data corresponding to various neural circuits, may be partitioned a training set for generating the ontology and fitting models, a validation set for optimizing model hyperparameters and selecting thresholds for the ontology, and a testing set for comparing the ontology against other mappings between neural circuits and mental functions (e.g., Research Domain Criteria (RDoC), Diagnostic and Statistical Manual (DSM), and/or the like).

In some example embodiments, the machine learning controller 114 may identify candidate domains for the ontology by applying an unsupervised learning approach that takes into account insights from information theory. For example, the machine learning controller 114 may identify links between the terms describing mental functions and the corresponding brain structures based on their co-occurrences across the training set. The machine learning controller 114 may reweight co-occurrence values by pointwise mutual information (PMI) in order to emphasize correlation between brain structure and mental function instead of the frequency the corresponding textual data and/or structural data in the corpus. For instance, although the term "face identification task" may be infrequent in article texts and few coordinates are mapped to the left amygdala, their co-occurrence may nevertheless be associated with a high PMI value because they are both observed in the same small subset of articles.

The machine learning controller 114 may determine the brain structures that support distinctive sets of mental functions by applying a clustering technique, such as k-means clustering, to group the brain structures by their PMI-weighted co-occurrences with mental function terms, for example, over a range of k values (e.g., 2 to 25). Moreover, the machine learning controller 114 may further identify the mental functions that are best representative of each brain structure based on prevalence rates across the corpus 125 at least because PMI gives high weight to connections that are specific but not necessarily common. For example, none of the top 25 terms with the strongest PMI-weighted co-occurrence with the left amygdala are present in more than 0.2% of articles included in the corpus. The top mental function terms (e.g., the top 25 terms) for each brain structure may be identified based on associations across the training set, computed as point-biserial correlations between binary term occurrences and the centroid of occurrences across the brain structures that are present in each neural circuit. Accordingly, for the neural circuit containing the left amygdala, the most strongly associated terms were "fear", "emotion", and "memory," which respectively occurred in 10.82%, 18.12%, and 17.74% of the articles included in the corpus.

In some example embodiments, the machine learning controller 114 may further apply a supervised learning strategy in order to optimize the number and size of domains in the ontology. For example, while up to 25 terms may be initially assigned to a given neural circuit, fewer terms may suffice in representing its functional repertoire. In order to identify the set of terms and structures with the strongest predictive relationships, the optimal number of mental function terms per circuit may be determined based on how well term occurrences predicted and were predicted by occurrences of structures over a range of mental function terms (e.g., 5 to 25 mental function terms). For instance, for each neural circuit, the machine learning controller 114 may fit a forward inference model (e.g., a multilayer neural network classifier) on the training set to predict the occurrence of brain structures based on the occurrence of various mental function terms. Furthermore, for each neural circuit, the machine learning controller 114 may fit a reverse inference model (e.g., a multilayer neural network classifier) on the training set to predict the occurrence of mental function terms based on the occurrence of various brain structures.

The machine learning controller 114 may select the optimal number of mental function terms for each neural circuit to maximize validation set performance averaged between the forward inference model and the reverse inference model. Likewise, the optimal number of domains may be established by the machine learning controller 114 training the forward inference model and the reverse inference model over the range of k values used to cluster brain structures into the corresponding neural circuits. For example, the forward inference model may be trained to predict the occurrence of brain structures for various neural circuits while the reverse inference model may be trained to predict the occurrence of mental function terms in various optimized word lists. The forward inference model and the reverse inference model may be evaluated based on the validation set, with the performance metrics averaged between the forward inference model and the reverse inference models at each level of k. Accordingly, the resulting ontology may include 6 domains that corresponds to non-overlapping circuits spanning the brain. Moreover, each domain may be associated with mental constructs that include one or more mental function terms. The mental function term with the highest degree centrality of its term-term co-occurrences may be used to identify each domain.

Figure 2A:
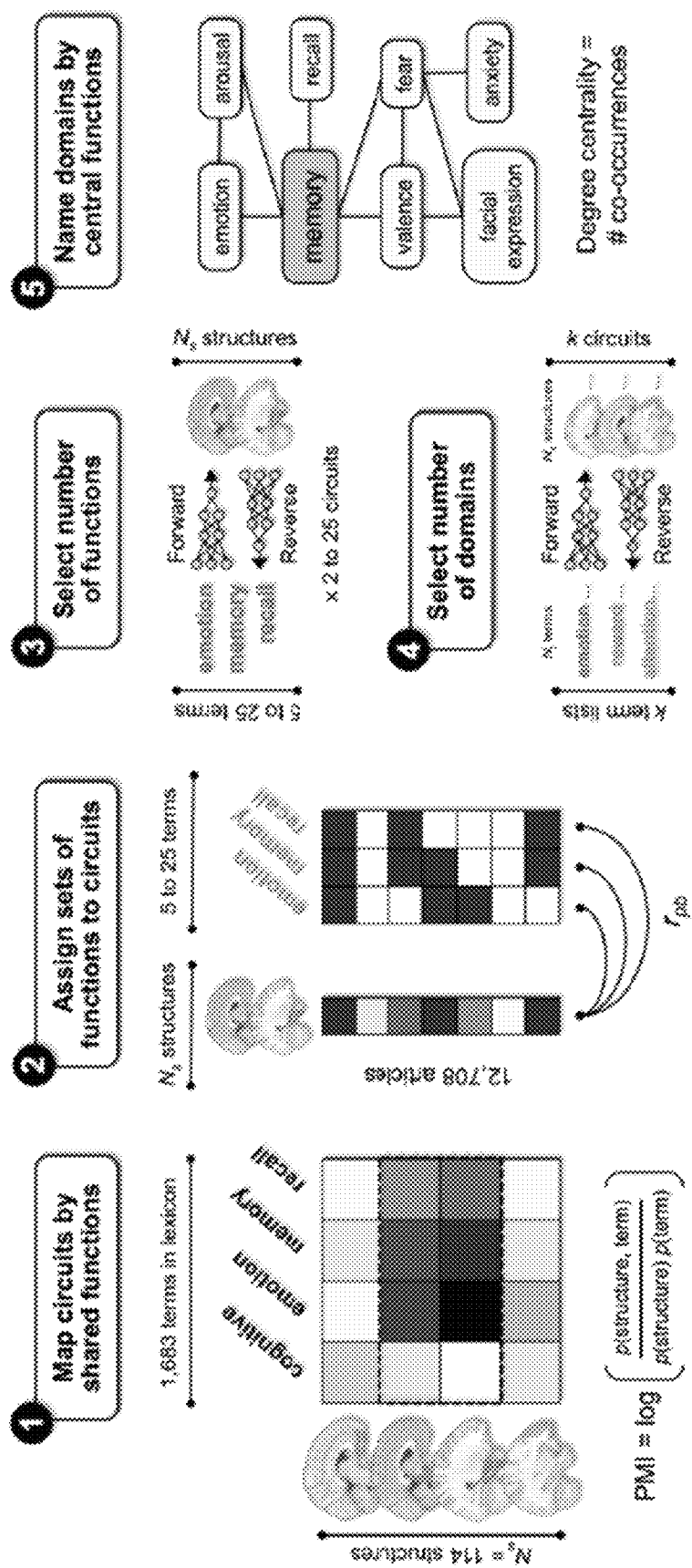
FIG. 2A depicts an example process for generating an ontology mapping brain structures to mental functions, in accordance with some example embodiments.

To further illustrate, FIG. 2A depicts an example of a process for generating an ontology that maps brain structures to mental functions, in accordance with some example embodiments. In the example shown in FIG. 2, 114 the ontology engine 110, for example, the machine learning controller 114, may cluster 114 brain structures by applying a k-means clustering algorithm (or another clustering algorithm) according to their co-occurrences with 1,683 terms for mental functions. The co-occurrence matrix may be weighted by pointwise mutual information (PMI) values before the top 25 terms for mental functions are assigned to the neural structure including each brain structure based on the point-biserial correlation ($r_{pb}$) of their binarized occurrences with the centroid of occurrences across structures.

An optimal number of mental function terms may be selected to maximize an average area under the receiver operating characteristic curve (ROC-AUC) of the forward inference model (e.g., neural network classifier) predicting brain structure occurrences from mental term occurrences and the reverse inference model (e.g., neural network classifier) predicting mental function term occurrences from brain structure occurrences over various lists of mental function terms that include 5 to 25 mental function terms. It should be appreciated that the ROC-AUC may provide a measure of the performance the underlying classifier in distinguishing between different classes. An optimal number of domains may be selected based on the average ROC-AUC of forward inference model as well as the reverse inference model. Occurrences may be summed across the mental function terms in each list and the brain structures in each neural circuit before thresholded by their mean across the articles in the corpus 125. As shown in FIG. 2A, each domain may be named by the mental function term with highest degree centrality of co-occurrences with other terms in the domain.

Figure 2B:
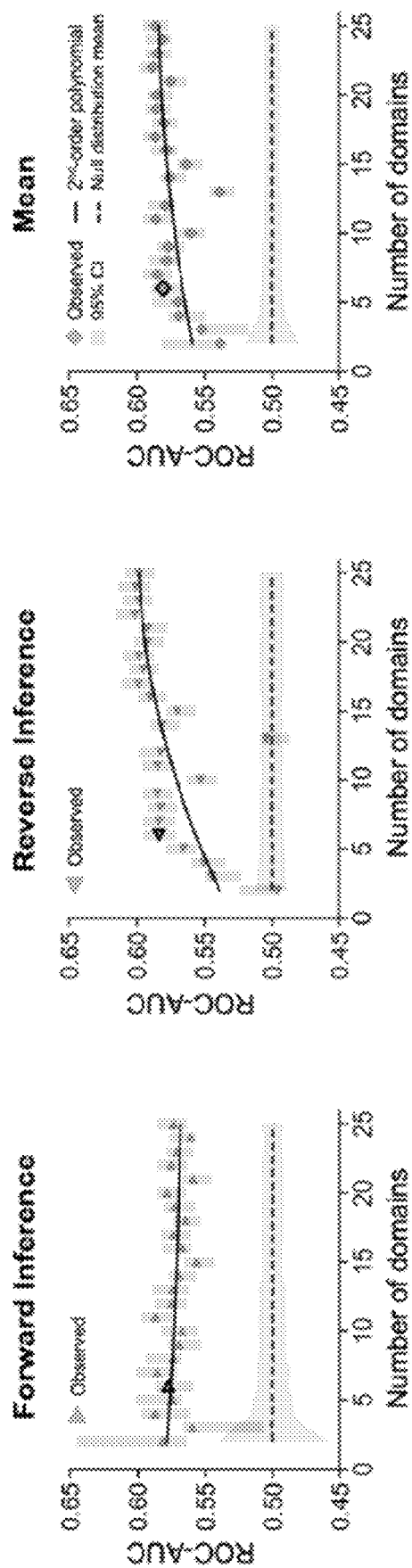
FIG. 2B depicts a performance of a forward inference model and a reverse inference model, in accordance with some example embodiments.

FIG. 2B depicts the performance of a forward inference model and a reverse inference model, in accordance with some example embodiments. In particular, FIG. 2B shows that the optimal number of domains in the ontology may be determined by the individual and average performance of the forward inference model and the reverse inference model as measured by the corresponding ROC-AUC. For example, FIG. 2 depicts the individual as well as average performance of the forward inference model and the reverse inference model when processing the validation set by plotting the respective ROC-AUC against the number of domains in the ontology. Markers are outlined in black for the k=6 solution, which was selected for the ontology as it was the lowest k value to achieve an average ROC-AUC along the asymptote. The shaded areas around markers represent 95% confidence intervals computed by resampling the articles in the validation set with replacement over 1,000 iterations. The dashed line represents the mean of null distributions generated by shuffling true labels for the validation set articles over 1,000 iterations, and the surrounding shaded area is the 95% confidence interval.

Figure 3A:
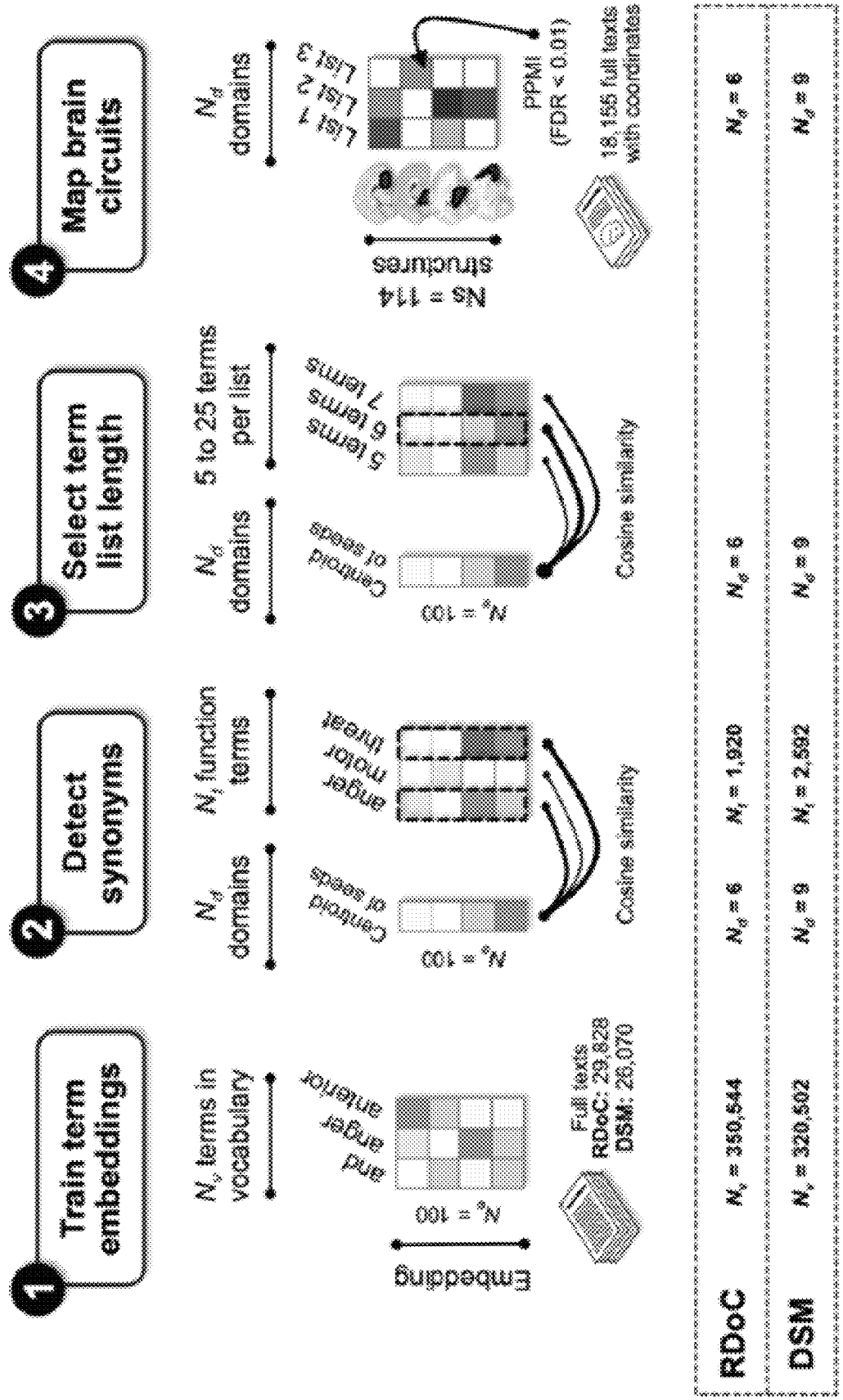
FIG. 3A depicts an example of a process for mapping expert-determined frameworks for brain function and mental illness, in accordance with some example embodiments.

The domains that form the ontology generated by the ontology engine 110 may be compared to the mental functions (and/or dysfunctions) identified in conventional expert-determined knowledge frameworks. In order to perform this comparison, expert determined frameworks for brain function (e.g., Research Domain Criteria (RDoC)) and psychiatric illness (e.g., Diagnostic and Statistical Manual (DSM)) may be mapped in a top-down fashion beginning with their terms for mental functions and dysfunction. As shown in FIG. 3A, one or more natural language processing (NPL) techniques may be applied to translate the language of the frameworks into the language of the human neuroimaging literature, and the resulting list of terms corresponding to mental functions may be mapped onto neural circuits containing one or more brain structures.

For example, the natural language processing may include embedding the text in the conventional expert-determined frameworks in order to identify candidate synonyms among the terms for mental function based on the cosine similarity of their embeddings to the centroid of seed embeddings in each domain. Doing so may yield synonyms with higher semantic similarity. Brain circuits may be mapped to each list of mental function terms based on PMI-weighted co-occurrences with brain structures across the full corpus of articles with coordinates (n=18,155 articles), restricting the circuits to positive values with FDR<0.01. This approach yielded the same number of circuits as there are domains in the expert-determined frameworks, with each domain corresponding to a circuit of co-occurring brain structures and being associated with 5 to 25 mental function terms. It should be appreciated that the identification of synonyms may be obviated when generating the data-driven ontology at least because the candidate mental function terms included in the data-driven ontology may be curated based on relevance to neuroimaging literature as well as relationship to spatial data (e.g., coordinates of various neural circuits). In doing so, the domains in the data-driven ontology may be defined jointly by mental functions as well as brain structures.

Referring again to FIG. 3A, terms from the expert-determined frameworks may be translated into the language of the human neuroimaging literature through a computational linguistics approach. First, word embeddings of length 100 may be trained using GloVe. For the mental function framework (e.g., Research Domain Criteria (RDoC)), the word embeddings may be trained on a general human neuroimaging corpus of 29,828 articles. For the psychiatric illness framework (e.g., Diagnostic and Statistical Manual (DSM)), the word embeddings may be trained on a psychiatric human neuroimaging corpus of 26,070 articles. Candidate synonyms included terms for mental functions in the case of RDoC and for both mental functions and psychopathology in the case of the DSM.

In the second step shown in FIG. 3A, the closest synonyms of seed terms may be identified based on the cosine similarity of synonym term embeddings with the centroid of embeddings across seed terms in each domain. Third, the number of terms for each domain may be selected to maximize cosine similarity with the centroid of seed terms. The mental function term lists for each domain may be mapped onto brain circuits based on positive pointwise mutual information (PPMI) of term and structure co-occurrences across the corpus of 18,155 articles with activation coordinate data. Brain structures were included in the circuit if the FDR of the observed PPMI was less than 0.01, determined by comparison to a null distribution generated by shuffling term list features over 10,000 iterations.

Figure 3B:
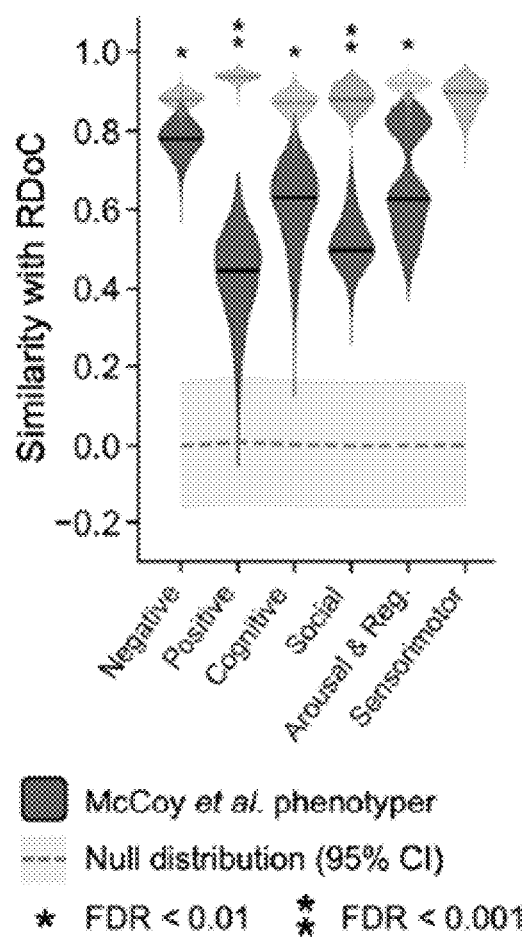
FIG. 3B depicts a graph comparing semantic similarity to seed terms in an expert determined framework and a baseline from literature, in accordance with some example embodiments.

Referring now to FIG. 3B, semantic similarity to seed terms in the RDoC framework for our term lists generated using GloVE (colored) may be compared to a baseline from the literature (dark gray). The baseline model may include lists of mental function terms generated through latent semantic analysis. Bootstrap distributions for each domain may be generated by resampling the 100-n embedding dimension with replacement over 10,000 iterations, then assessed for a difference in means (*FDR<0.01, FDR<0.001). The solid lines shown in FIG. 3B may denote the observed similarity values. Null distributions may be generated for the GloVe term lists by shuffling embeddings over 10,000 iterations. The dashed line shown in FIG. 3B** may denote the null distribution means.

Figure 4A:
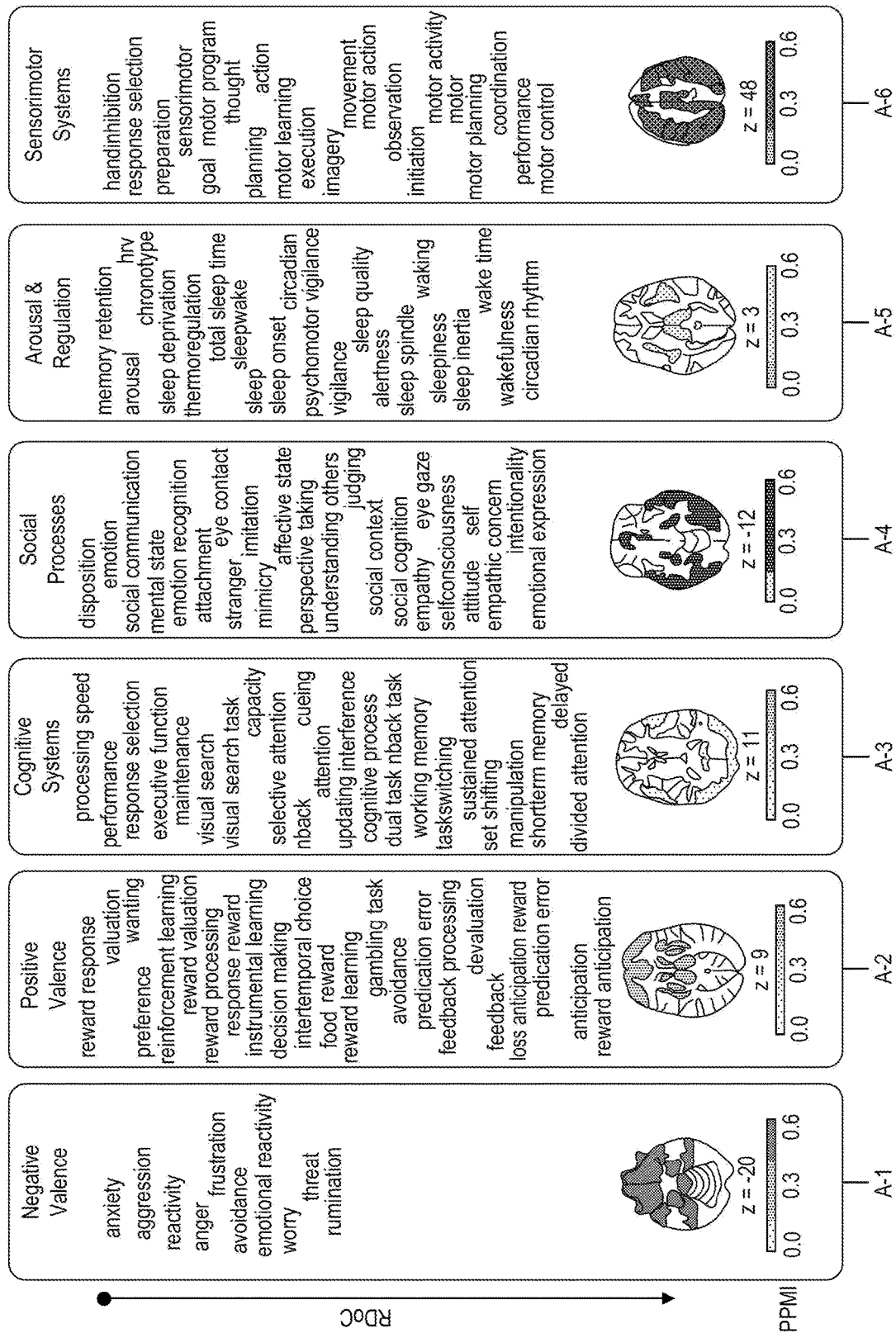
FIG. 4A-FIG. 4C depicts links between a data-driven ontology of brain functions and expert-determined frameworks for brain function and mental illness, in accordance with some example embodiments.
Figure 4B:
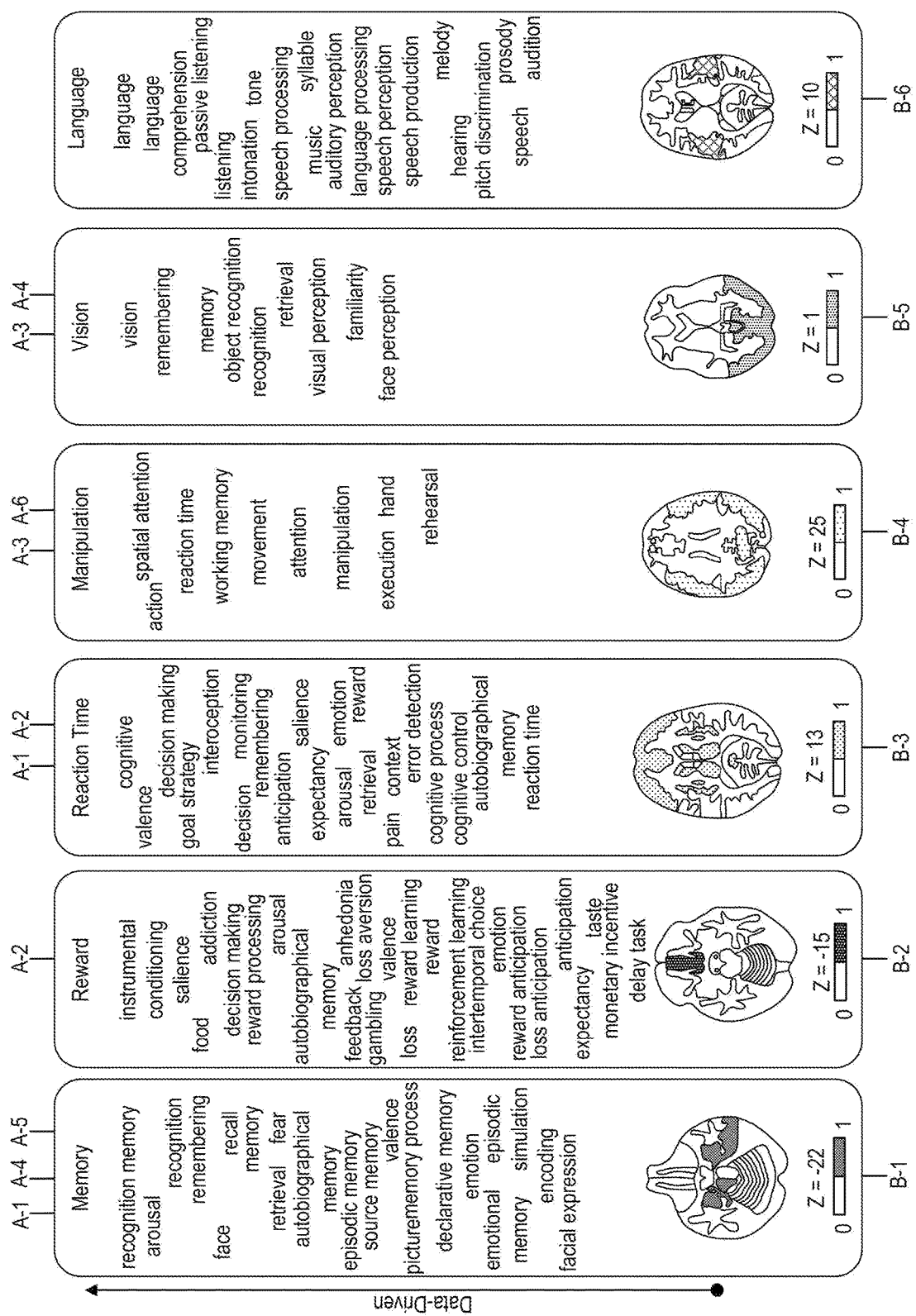
Figure 4C:
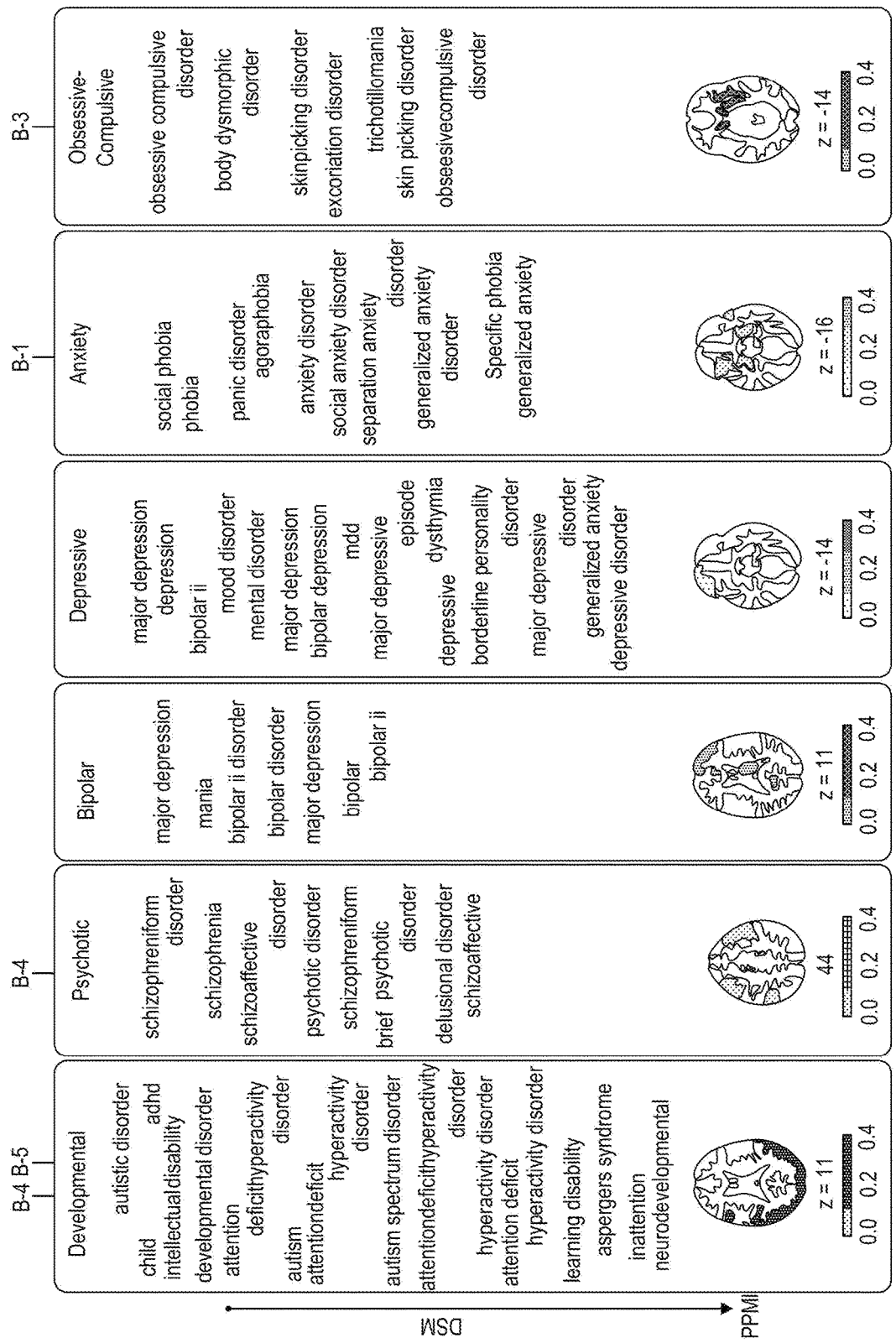
Figure 5:
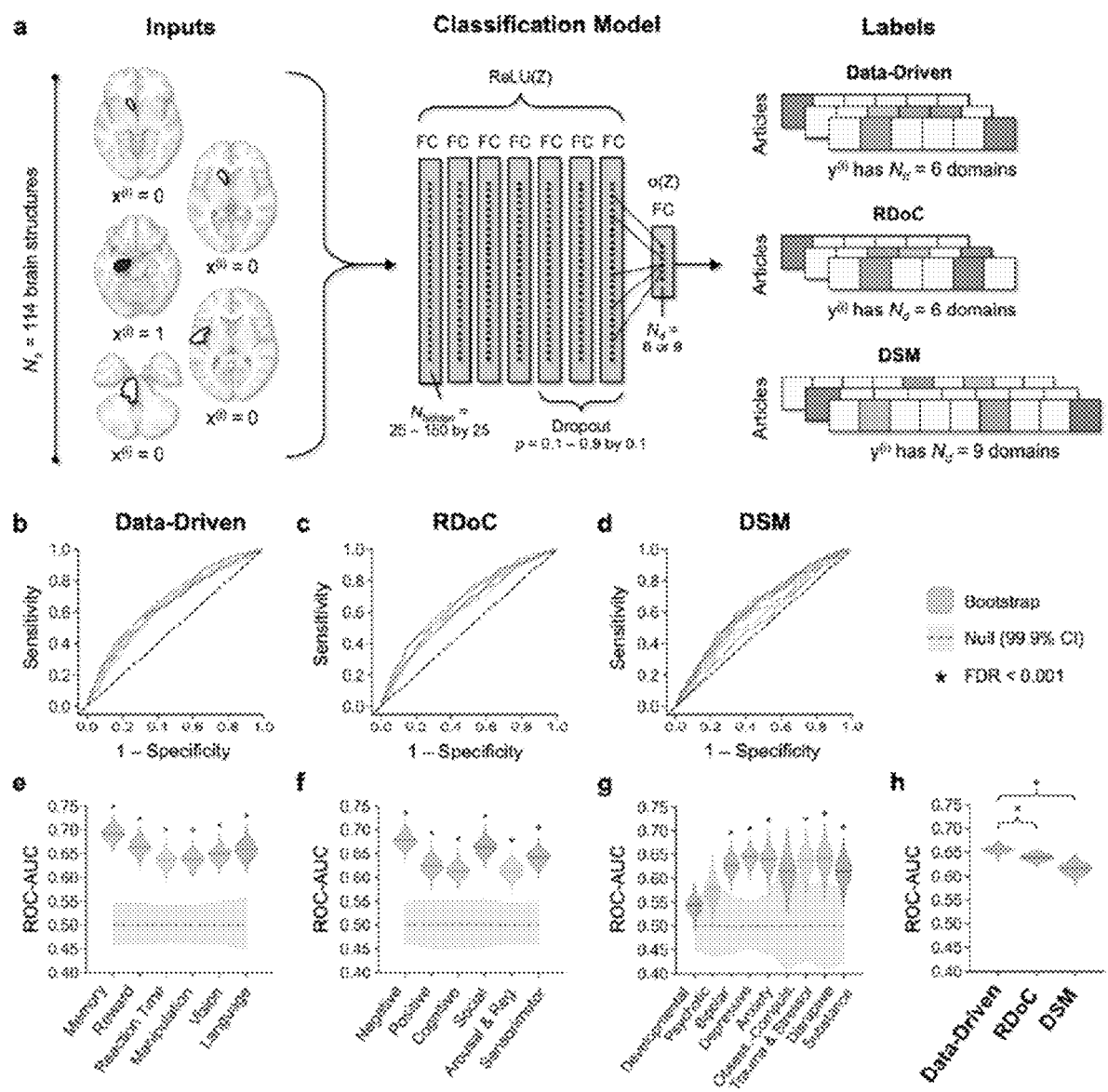
FIG. 5 depicts the reproducibility of a data-driven ontology, in accordance with some example embodiments.
Figure 6:
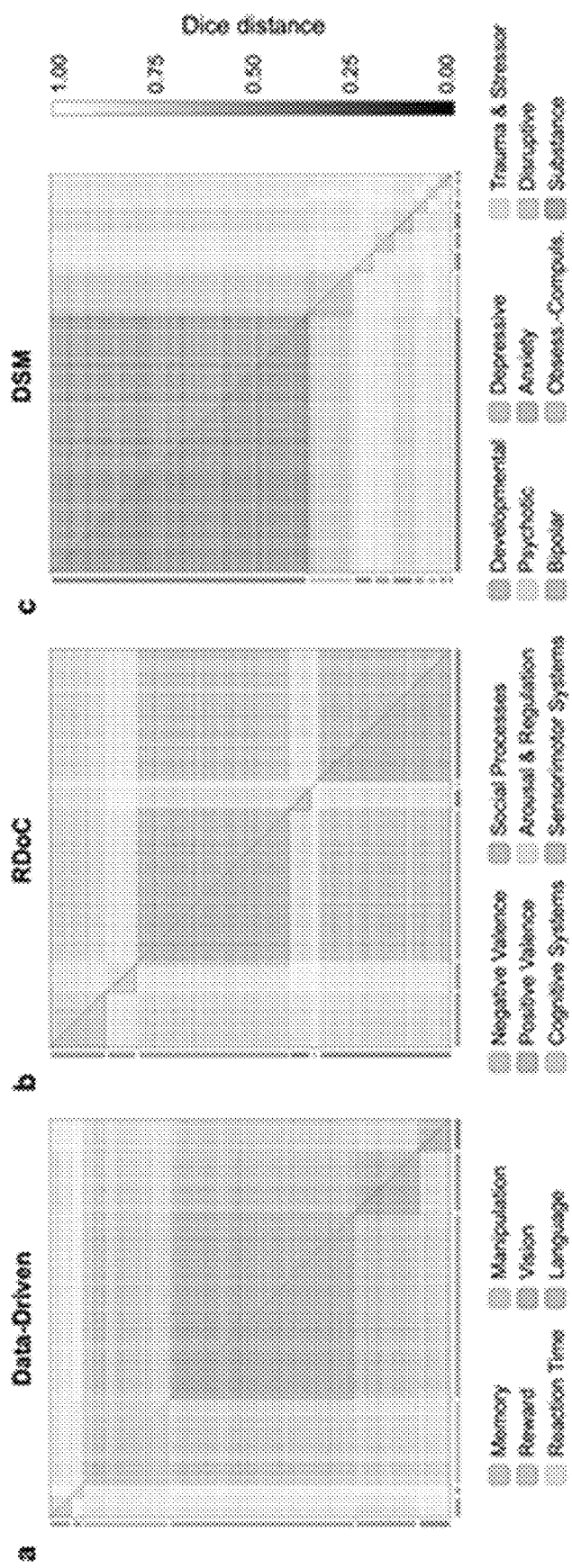
FIG. 6 depicts articles partitioned by similarity to mental functions and brain circuits in the domains of various frameworks, in accordance with some example embodiments.
Figure 7:
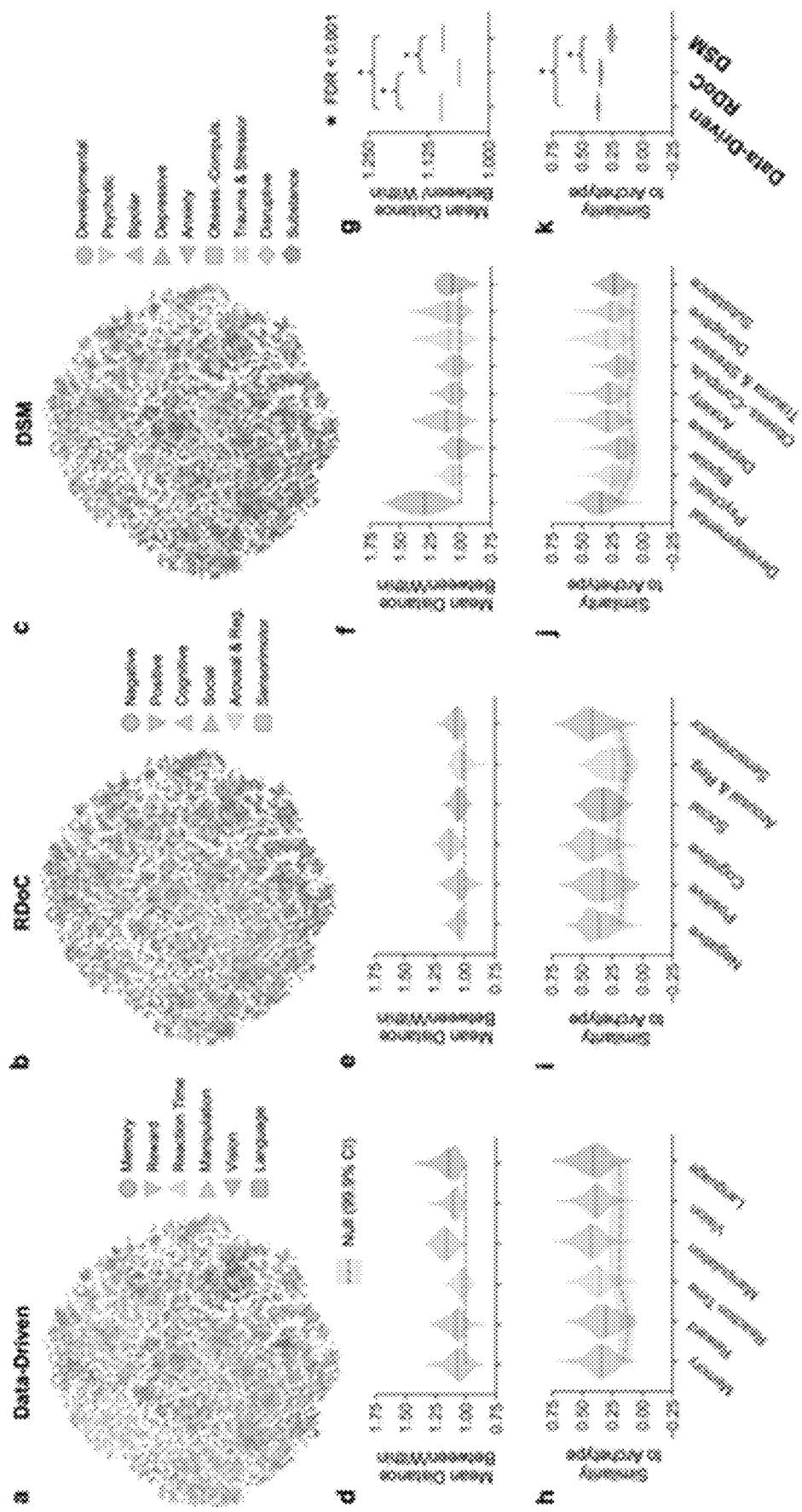
FIG. 7 depicts the modularity of a data-driven ontology, in accordance with some example embodiments.

FIG. 4 depicts notable differences between the ontology derived by the ontology engine 110 and the expert-determined frameworks. Referring to FIG. 4, the links shown may be scaled to the Dice similarity of mental function terms and brain structures in each domain (FDR<0.05). Word size may be scaled to frequency in the corpus of 18,155 articles with activation coordinate data. At FIG. 4*a*, the expert-determined framework for brain function may be modeled in a top-down manner from terms to brain circuits. At FIG. 4*b*, an ontology for brain function may be generated by the ontology engine 110 in a bottom-up manner beginning with brain circuitry. Finally, at FIG. 4c, the expert-determined framework for mental disorders may be modeled in a top-down manner by a procedure analogous to that for the expert-determined framework for brain function.

Referring again to FIG. 4, the first notable difference is that the ontology derived by the ontology engine 110 may offer novel combinations of emotional and cognitive terms in its domains for Memory and Reaction Time, which each relate to several domains in the expert-determined frameworks. Likewise, the domain in the expert-determined framework for Cognitive Systems may relate strongly to both Vision and Manipulation in the ontology generated by the ontology engine 110, indicating that further functional specification may be warranted in expert-determined frameworks. While the Reward domain of the ontology is similar to a single expert-determined domain for Positive Valence at the FDR<0.05 threshold, the Reward circuitry may be defined more specifically by frontomedial regions and the nucleus accumbens. Finally, the ontological domain for Language lacks above-threshold similarity with expert-determined frameworks, implying that it has been largely omitted from characterizations of brain function and mental illness in the expert-determined frameworks.

The ontology generated by the ontology engine 110 may also be evaluated against conventional expert-determined frameworks in terms of reproducibility, modularity, and generalizability. Reproducibility concerns whether the circuit-function links underlying domains are well predicted from their observed co-occurrences in the corpus 125. Human neuroimaging has demonstrated that several brain regions (e.g., the insula and anterior cingulate) are widely activated across task contexts, rendering them unreliable predictors of mental state. If links between brain circuits and mental functions are not reproducible across studies, then the ontological entities and neuropsychiatric biomarkers derived from them will be of limited utility.

As shown in FIG. 4a, the reproducibility of circuit-function links may be assessed based on the performance of multilayer neural network classifiers predicting mental functions in article texts from coordinate data mapped to various brain structures. Binary scores for the mental functions listed under each domain were computed by mean-thresholding term occurrences, then mean-thresholding the sum of terms within each domain list. Hyperparameters were tuned on the validation set of 20% of articles from the corpus 125, and classifiers were evaluated by area under the receiver operating characteristic curve (ROC-AUC) in the test set containing 10% of articles (n=1,816; FIGS. 4b-g). FIG. 4b shows that ROC-AUC was higher across domains of the data-driven ontology as compared to RDoC and the DSM. Contrastingly, FIG. 4f shows that whereas all domains of the data-driven and RDoC frameworks achieved above-chance ROC-AUC, the Developmental and Psychotic domains in the DSM framework did not. These results indicate that orienting neurobiological and psychiatric frameworks around the circuits and term lists derived through our data-driven approach could improve the reproducibility of their structure-function links. Further results supporting this conclusion were obtained when reproducibility analyses were repeated with classifiers that used mental function terms to predict occurrences of brain structures.

The second organizing principle of interest in constructing an ontology of brain function is modularity which corresponds to the extent to which domains are internally homogeneous and distinctive from one another in their patterns of functions and structures. The principle of modulatory has been observed across neural measures and scales, ranging from single neurons to distributed resting-state fMRI networks in humans. However, because task-based neuroimaging studies are limited in the number of mental states they can reasonably induce, it is largely unknown whether task-related brain activity is similarly modular. An automated meta-analytic approach may overcome this limitation to the extent one can assume that articles reporting different mental constructs and brain structures in their texts and data are studying different underlying domains of brain function. For example, as shown in FIG. 7a-g, articles may be assigned to the most similar domain of each framework, yielding "subfields" of human neuroimaging. Consistent with high comorbidity rates and similar neural alterations between affective disorders, there is visible overlap among the Bipolar, Depressive, and Anxiety illness domains of the DSM.

Modularity may be assessed by the ratio of mean Dice distance of articles between versus within subfields. The domain-level results exceeded chance for all domains across the three frameworks. Macro-averaging across domains in each framework, we find that modularity is higher for the data-driven ontology compared to both RDoC and the DSM. These results support the movement currently underway to ground psychiatric diagnoses in brain circuits for transdiagnostic mental constructs, while at the same time cautioning against the assumption that expert-determined domains of brain function will lead to improved ontological modularity.

The third principle of central relevance to an ontology of brain function is generalizability. By this principle, the pattern of functions and structures included in each domain of the ontology should be a representative archetype of the functions and structures occurring in single articles, and presumably, in the underlying neurobiological phenomena they address. Previous meta-analyses have demonstrated that some (though not all) psychological domains have generalizable representations in the activity of specialized brain regions. FIG. 7h-k, generalizability may be determined by computing the similarity of function and structure occurrences in each article to the archetypal function-structure pattern of the domain to which it was assigned. Similarity to the archetype exceeded chance for all frameworks tested, supporting the interpretation that they represent information which generalizes well within the subfields of human neuroscience. Yet, further gains in similarity to the archetype across domains were achieved by both the data-driven ontology and RDoC relative to the DSM, highlighting the disconnect between current understanding of brain function and the way that mental disorders have historically been categorized. If mental disorders were redefined as disruptions in basic brain circuitry, their information content may better generalize within subfields of the human neuroscience literature.

In some example embodiments, the ontology generated by the ontology engine 110 may be applied to one or more electronic medical records. Each electronic medical record may include textual data describing diagnoses, encounters, procedures, laboratory finding, and/or the like. The ontology may be applied to phenotype the electronic medical record of a patient including by quantitatively rating the medical record along various domains of the ontology (e.g., emotion, retrieval, language, arousal, movement, and/or the like). As used herein, phenotyping an electronic medical record may include determining, based on the content of the electronic medical record, one or more observable characteristics of the patient associated with the electronic medical record. More broadly, phenotyping refers to identifying any meaningful and/or consistent characteristic of individuals that describes a useful feature to understand about them. Phenotyping may be retrospective (e.g., historical characteristics), clinical, behavioral, reflect patterns of use of resources or interventions, prospective (e.g., related to a particular future clinical course), or with respect to biological/physiological characteristics or reactions. The quantitative measures of psychopathology may be used to predict clinical outcomes for the patient including, for example, a duration of hospital stay, a quantity of emergency room (ER) visits, a quantity of office visits, healthcare cost, prescriptions, refills, comorbid conditions, and/or the like. An example phenotype of interest may be that of a patient with repeated hospitalizations in a given period, or alternatively with consistent medication refills but few or no clinical visits. Such extremes might characterize a phenotype of treatment responsiveness.

Figure 8:
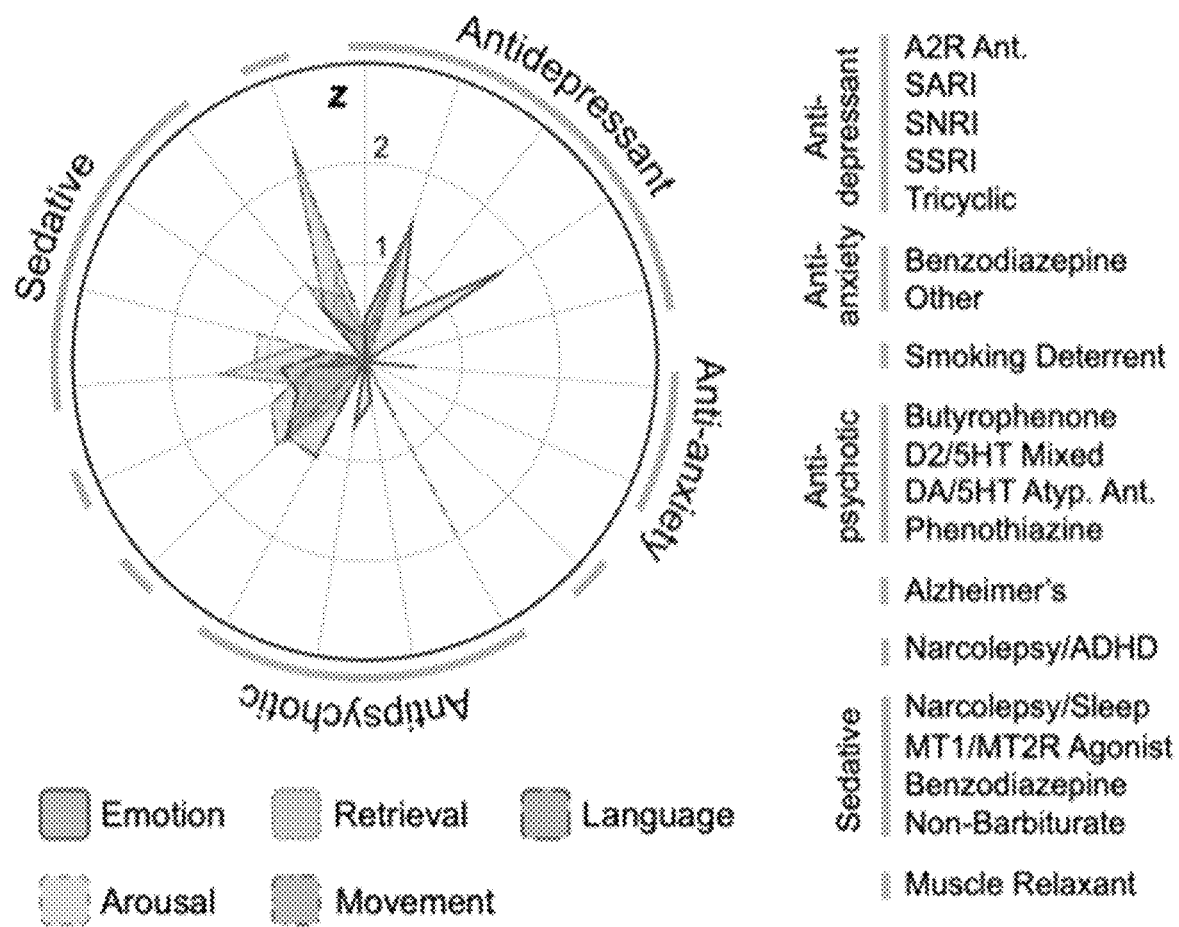
FIG. 8 depicts a psychotropic prescription profile for the psychopathology dimensions of a data-driven ontology, in accordance with some example embodiments.

In some example embodiments, phenotyping of an electronic medical record based on the ontology may include determining, for each domain of the ontology, a rating corresponding to a proportion of mental function terms associated with the domain that is present in the electronic medical record. As shown in FIG. 8, the domains of the ontology (e.g., emotion, retrieval, language, arousal, movement, and/or the like) may be characterized by their patterns of associated psychotropic medications. The $r_{pb}$ may be computed between continuous ratings of psychopathology in patient notes and binary measures of whether or not a medication of each psychotropic pharmaceutical class had ever been prescribed in the available patient history. FIG. 8 shows the z-scored $r_{pb}$ between psychopathology dimension scores and whether a patient was prescribed a psychotropic medication at any point in the available medical history. Medications may be grouped by pharmaceutical class. For example, the list of medications may correspond to the radial lines of the polar plot beginning at the top center and proceeding clockwise.

A crucial test of the ontology in phenotyping electronic medical records may be whether its domains are predictive of relevant clinical endpoints. In particular, high ratings for a domain may be linked to a clinical outcome if the coefficient for that domain is significantly greater than zero in a linear regression model predicting a quantitative variable for the outcome. For example, two outcomes of interest in psychiatry are emergency room admissions and hospital stays, which incur high costs and may require extreme treatment measures. These negative outcomes might be more effectively prevented if their causes were better understood.

To assess the predictive value of the dimensional ratings of psychopathology generated by applying the ontology to phenotype an electronic medical record, linear regression models may be fit to predict the quantity of emergency room visits and total duration of hospital stay for patients that were subsequently admitted. Table 3 below depicts the coefficients for predictors of clinical outcomes associated with the ontology generated by the ontology engine 110. As shown in Table 3, the Emotion and Retrieval domains may have positive coefficients in models predicting emergency room visits and duration of hospital stay. Accordingly, the Emotion and Retrieval domains may be linked to these outcomes. The coefficients are greater than zero with 95% confidence as determined by fitting the models to random samples of notes taken with replacement.

TABLE 3

| | Data-Driven | | | |
|---|---|---|---|---|
| | Number of ER Visits (n = 7,791) | | Duration of Hospital Stay (n = 2,572) | |
| | β (95% CI) | FDR | β (95% CI) | FDR |
| Emotion | 11.90 (8.16 to 15.63) | <0.0001 | 67.74 (43.77 to 92.46) | <0.0001 |
| Retrieval | 9.01 (5.25 to 12.83) | <0.0001 | 74.81 (48.03 to 102.11) | <0.0001 |
| Language | −8.21 (−13.23 to −3.13) | 0.0062 | −66.01 (−98.07 to −34.33) | 0.00016 |
| Arousal | 0.44 (−3.13 to 4.02) | 0.42 | 3.41 (−19.99 to 26.42) | 0.41 |
| Movement | 20.87 (17.49 to 24.25) | <0.0001 | −0.10 (−0.14 to −0.07) | <0.0001 |
| Age | −0.01 (−0.01 to 0.00) | 0.11 | −0.10 (−0.14 to −0.07) | <0.0001 |
| Gender (Male) | −0.18 (−0.46 to 0.11) | 0.21 | 1.36 (−0.86 to 3.52) | 0.20 |
| Race (White) | −0.13 (−0.42 to 0.16) | 0.27 | −1.33 (−3.73 to 0.96) | 0.20 |

Figure 9:
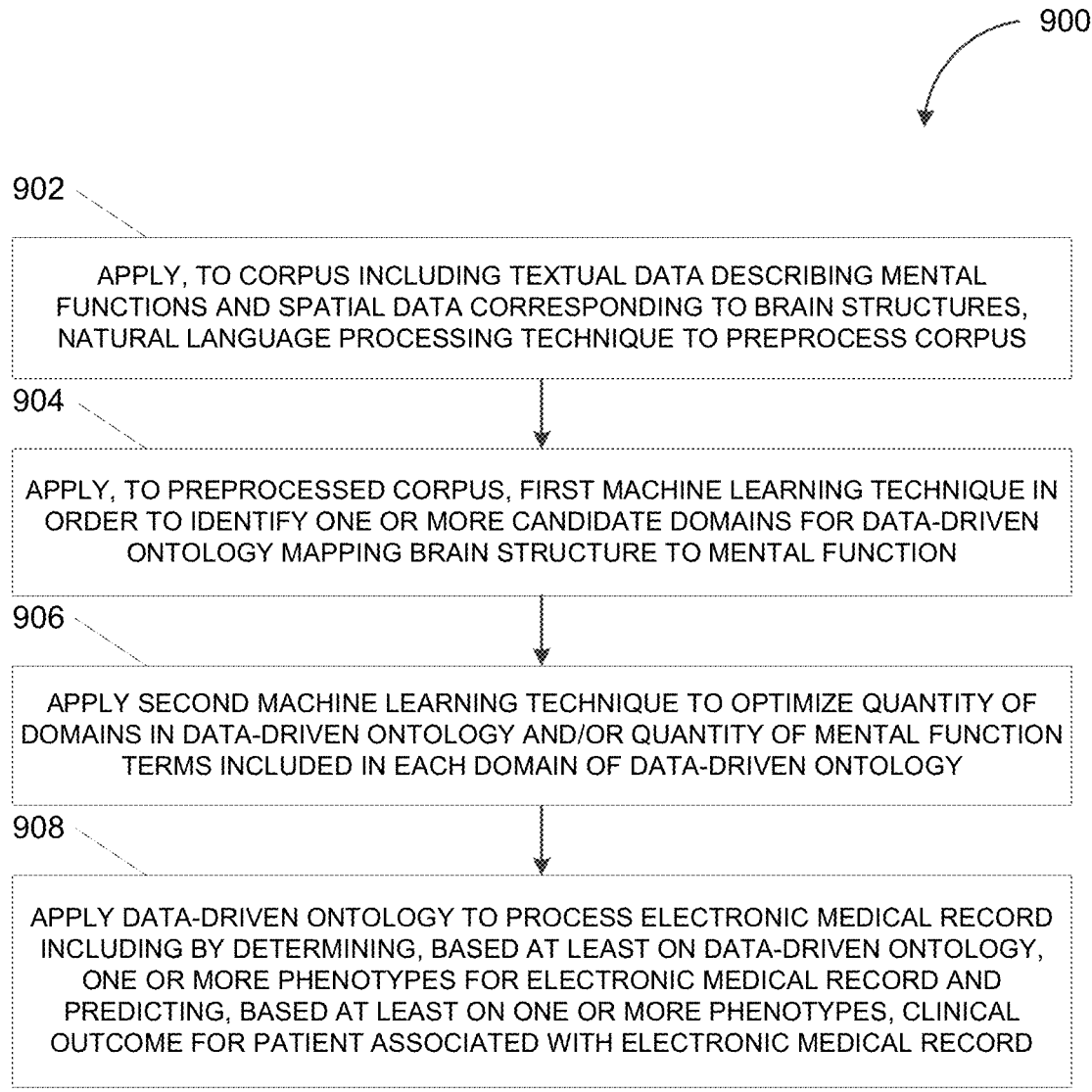
FIG. 9 depicts a flowchart illustrating an example of a process for a data-driven ontology, in accordance with some example embodiments.

FIG. 9 depicts a flowchart illustrating an example of a process 900 for a data-driven ontology, in accordance with some example embodiments. Referring to FIGS. 1 and 9, the ontology engine 110 may perform the process 900 in order to generate and apply a data-driven ontology mapping brain structure to mental functions.

The ontology engine 110 may apply, to a corpus including textual data describing mental functions and spatial data corresponding brain structures, a natural language technique to preprocess the corpus (902). For example, the ontology engine 110 may be configured to preprocess each of the articles included in the corpus 125, each of which textual data describing mental functions as well as the spatial data corresponding to various neural circuits. The processing may include case-folding, removal of stop words and punctuation, lemmatization (e.g., with WordNet), and/or the like. The preprocessed articles from the corpus 125 may be partitioned a training set for generating the ontology and fitting models, a validation set for optimizing model hyper-parameters and selecting thresholds for the ontology, and a testing set for comparing the ontology against other mappings between neural circuits and mental functions (e.g., Research Domain Criteria (RDoC), Diagnostic and Statistical Manual (DSM), and/or the like).

The ontology engine 110 may apply, to the processed corpus, a first machine learning technique to identify one or more candidate domains for a data-driven ontology mapping brain structure to mental function (904). In some example embodiments, may identify candidate domains for the ontology by applying an unsupervised learning approach that takes into account insights from information theory. For example, the ontology engine 110 may identify candidate domains, which links the terms describing mental functions and the corresponding brain structures, based on the co-occurrence of mental function terms and brain structures across the training set. Co-occurrence values may be reweighted by pointwise mutual information (PMI) in order to emphasize correlation between brain structure and mental function instead of the frequency the corresponding textual data and/or structural data in the corpus. The brain structures that support distinctive sets of mental functions by be identified by applying a clustering technique, such as k-means clustering, to group the brain structures by their PMI-weighted co-occurrences with mental function terms, for example, over a range of k values (e.g., 2 to 25). The ontology engine 110 may further identify the mental functions that are best representative of each brain structure based on prevalence rates across the corpus 125 at least because PMI gives high weight to connections that are specific but not necessarily common.

The ontology engine 110 may apply a second machine learning technique to optimize a quantity of domains in the data-driven ontology and/or a quantity of mental function terms included in each domain of the data-driven ontology (906). In some example embodiments, the ontology engine 110 may apply a supervised learning strategy in order to optimize the number and size of domains in the ontology. For example, in order to identify the set of terms and structures with the strongest predictive relationships, the optimal number of mental function terms per circuit may be determined based on how well term occurrences predicted and were predicted by occurrences of structures over a range of mental function terms (e.g., 5 to 25 mental function terms). As such, for each neural circuit, the ontology engine 110 may fit a forward inference model (e.g., a multilayer neural network classifier) on the training set to predict the occurrence of brain structures based on the occurrence of various mental function terms. Furthermore, for each neural circuit, the ontology engine 110 may fit a reverse inference model (e.g., a multilayer neural network classifier) on the training set to predict the occurrence of mental function terms based on the occurrence of various brain structures.

The ontology engine 110 may apply the data-driven ontology to process an electronic medical record including by determining, based at least on the data-driven ontology, one or more phenotypes for the electronic medical record and predicting, based at least on the one or more phenotypes, a clinical outcome for a patient associated with the electronic medical record (908). For example, the electronic medical record may include textual data describing diagnoses, encounters, procedures, laboratory finding, and/or the like. Phenotyping the electronic medical record may include identifying one or more domains in the data-driven ontology (e.g., emotion, retrieval, language, arousal, movement, and/or the like) that align with the contents of the medical record. Accordingly, phenotyping of the electronic medical record based on the data-driven ontology may include determining, for each domain of the ontology, a rating corresponding to a proportion of mental function terms associated with the domain that is present in the electronic medical record. The highest rated domains and/or domains having an above-threshold rating may be determined to correspond to the phenotypes, for example, the observable characteristics, of a patient associated with the electronic medical record. Moreover, these phenotypes may be used to determine a clinical outcome for the patient including, for example, a duration of hospital stay, a quantity of emergency room (ER) visits, a quantity of office visits, healthcare cost, prescriptions, refills, comorbid conditions, and/or the like.

Figure 10:
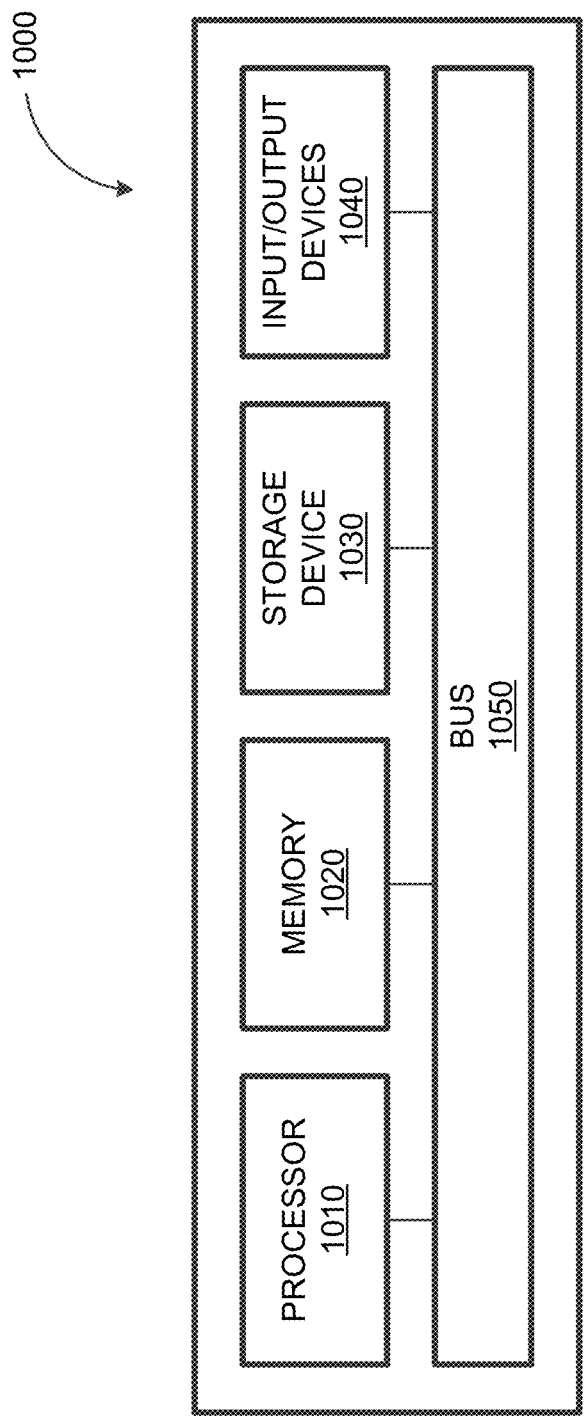
FIG. 10 depicts a block diagram illustrating a computing system, in accordance with some example embodiments.

FIG. 10 depicts a block diagram illustrating a computing system 1000 consistent with some implementations of the current subject matter. Referring to FIGS. 1 and 10, the computing system 1000 can be used to implement the ontology engine 110 and/or any components therein.

As shown in FIG. 10, the computing system 1000 can include a processor 1010, a memory 1020, a storage device 1030, and input/output devices 1040. The processor 1010, the memory 1020, the storage device 1030, and the input/output devices 1040 can be interconnected via a system bus 1050. The processor 1010 is capable of processing instructions for execution within the computing system 1000. Such executed instructions can implement one or more components of, for example, the ontology engine 110. In some implementations of the current subject matter, the processor 1010 can be a single-threaded processor. Alternately, the processor 1010 can be a multi-threaded processor. The processor 1010 is capable of processing instructions stored in the memory 1020 and/or on the storage device 1030 to display graphical information for a user interface provided via the input/output device 1040.

The memory 1020 is a computer readable medium such as volatile or non-volatile that stores information within the computing system 1000. The memory 1020 can store data structures representing configuration object databases, for example. The storage device 1030 is capable of providing persistent storage for the computing system 1000. The storage device 1030 can be a floppy disk device, a hard disk device, an optical disk device, or a tape device, or other suitable persistent storage means. The input/output device 1040 provides input/output operations for the computing system 1000. In some implementations of the current subject matter, the input/output device 1040 includes a keyboard and/or pointing device. In various implementations, the input/output device 1040 includes a display unit for displaying graphical user interfaces.

According to some implementations of the current subject matter, the input/output device 1040 can provide input/output operations for a network device. For example, the input/output device 1040 can include Ethernet ports or other networking ports to communicate with one or more wired and/or wireless networks (e.g., a local area network (LAN), a wide area network (WAN), the Internet).

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example, as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive track pads, voice recognition hardware and software, optical scanners, optical pointers, digital image capture devices and associated interpretation software, and the like.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A computer-implemented method, comprising:
applying, to a corpus of data, a first machine learning technique to identify one or more candidate domains of an ontology mapping brain structure to mental function, the corpus of data including textual data describing a plurality of mental functions and spatial data corresponding to a plurality of brain structures, and the ontology including a plurality of domains each of which (1) corresponding to a neural circuiting including one or more brain structures and including (2) one or more mental function terms associated with the one or more brain structures;
applying a second machine technique to optimize a quantity of domains included in the ontology and/or a quantity of mental function terms included in each of the plurality of domains, the second machine learning technique including a forward inference model trained to predict an occurrence of a brain structure based on an occurrence various quantities of mental function term, and the second machine learning technique further including a reverse inference model trained to predict the occurrence of the various quantities of mental function terms based on the occurrence of a brain structure; and
applying the ontology to process an electronic medical record.

2. The method of claim 1, wherein the first machine learning technique comprises an unsupervised machine learning technique, and wherein the second machine learning technique comprises a supervised machine learning technique.

3. The method of claim 1, wherein the first machine learning technique comprises a k-means clustering algorithm configured to cluster the plurality of brain structures include in the corpus of data based at least on a co-occurrence value between each of the plurality of brain structures and each of the plurality of mental function terms.

4. The method of claim 3, wherein the co-occurrence value corresponds to a frequency at which a brain structure and a mental function term appear in a same article in the corpus of data, and wherein the co-occurrence value is further weighted based on a pointwise mutual information (PMI) corresponding to a probability that the brain structure and the mental function term appear in the same article.

5. The method of claim 1, wherein an optimal quantity of domains in the ontology and/or an optimal quantity of mental function terms included in each of the plurality of domains are selected to maximize a performance of the forward inference model and/or a performance of the reverse inference model.

6. The method of claim 5, wherein the performance of the forward inference model and/or the performance of the reverse inference model comprise an average area under the receiver operating characteristic curve (ROC-AUC).

7. The method of claim 1, wherein the forward inference model and/or the reverse inference model comprise a multilayer neural network classifier.

8. The method of claim 1, further comprising:
applying a natural language processing (NLP) technique to preprocess the corpus of data prior to applying the first machine learning technique, the preprocessing includes one or more of a case-folding, a removal of stop words and punctuation, and a lemmatization.

9. The method of claim 1, wherein the electronic medical record is processed by at least determining, based at least on the ontology, one or more phenotypes associated with the electronic medical record and (2) predicting, based at least on the one or more phenotypes, a clinical outcome for a patient associated with the electronic medical record.

10. The method of claim 9, wherein the one or more phenotypes for the electronic medical record may be determined by at least determining, for each of the plurality of domains of the ontology, a rating corresponding to a proportion of mental function terms associated with the domain that is present in the electronic medical record, and wherein the one or more phenotypes correspond to one or more highest rated domains and/or one or more domains having an above-threshold rating.

11. The method of claim 9, wherein the clinical outcome includes a duration of hospital stay, a quantity of office visits, a quantity of emergency room visits, healthcare cost, prescriptions, refills, comorbid conditions, and/or the like.

12. The method of claim 1, wherein the plurality of domains include emotion, retrieval, language, arousal, and movement.

13. A system, comprising:
at least one data processor; and
at least one memory storing instructions, which when executed by the at least one data processor, result in operations comprising:
applying, to a corpus of data, a first machine learning technique to identify one or more candidate domains of an ontology mapping brain structure to mental function, the corpus of data including textual data describing a plurality of mental functions and spatial data corresponding to a plurality of brain structures, and the ontology including a plurality of domains each of which (1) corresponding to a neural circuiting including one or more brain structures and including (2) one or more mental function terms associated with the one or more brain structures;
applying a second machine technique to optimize a quantity of domains included in the ontology and/or a quantity of mental function terms included in each of the plurality of domains, the second machine learning technique including a forward inference model trained to predict an occurrence of a brain structure based on an occurrence various quantities of mental function term, and the second machine learning technique further including a reverse inference model trained to predict the occurrence of the various quantities of mental function terms based on the occurrence of a brain structure; and
applying the ontology to process an electronic medical record.

14. The system of claim 13, wherein the first machine learning technique comprises an unsupervised machine learning technique, and wherein the second machine learning technique comprises a supervised machine learning technique.

15. The system of claim 13, wherein the first machine learning technique comprises a k-means clustering algorithm configured to cluster the plurality of brain structures include in the corpus of data based at least on a co-occurrence value between each of the plurality of brain structures and each of the plurality of mental function terms, and wherein the co-occurrence value corresponds to a frequency at which a brain structure and a mental function term appear in a same article in the corpus of data, and wherein the co-occurrence value is further weighted based on a pointwise mutual information (PMI) corresponding to a probability that the brain structure and the mental function term appear in the same article.

16. The system of claim 13, wherein an optimal quantity of domains in the ontology and/or an optimal quantity of mental function terms included in each of the plurality of domains are selected to maximize a performance of the forward inference model and/or a performance of the reverse inference model.

17. The system of claim 13, wherein the electronic medical record is processed by at least determining, based at least on the ontology, one or more phenotypes associated with the electronic medical record and (2) predicting, based at least on the one or more phenotypes, a clinical outcome for a patient associated with the electronic medical record.

18. A non-transitory computer readable medium storing instructions, which when executed by at least one data processor, result in operations comprising:
applying, to a corpus of data, a first machine learning technique to identify one or more candidate domains of an ontology mapping brain structure to mental function, the corpus of data including textual data describing a plurality of mental functions and spatial data corresponding to a plurality of brain structures, and the ontology including a plurality of domains each of which (1) corresponding to a neural circuiting including one or more brain structures and including (2) one or more mental function terms associated with the one or more brain structures;
applying a second machine technique to optimize a quantity of domains included in the ontology and/or a quantity of mental function terms included in each of the plurality of domains, the second machine learning technique including a forward inference model trained to predict an occurrence of a brain structure based on an occurrence various quantities of mental function term, and the second machine learning technique further including a reverse inference model trained to predict the occurrence of the various quantities of mental function terms based on the occurrence of a brain structure; and
applying the ontology to process an electronic medical record.

* * * * *